(12) United States Patent
Northrop

(10) Patent No.: US 10,524,490 B2
(45) Date of Patent: Jan. 7, 2020

(54) PROCESS AND METHOD FOR OPTIMIZING PRODUCTION OF FOOD AND FEED

(71) Applicant: Timberfish, LLC, Amherst, NY (US)

(72) Inventor: Jere Northrop, Amherst, NY (US)

(73) Assignee: Timberfish, LLC, Amherst, NY (US)

( * ) Notice: Subject to any disclaimer, the term of this patent is extended or adjusted under 35 U.S.C. 154(b) by 98 days.

(21) Appl. No.: 15/599,954

(22) Filed: May 19, 2017

(65) Prior Publication Data

US 2017/0265440 A1    Sep. 21, 2017

Related U.S. Application Data

(63) Continuation of application No. 13/580,299, filed as application No. PCT/US2011/026266 on Feb. 25, 2011, now Pat. No. 9,681,644.

(Continued)

(51) Int. Cl.
| | |
|---|---|
| *A23K 50/30* | (2016.01) |
| *C12M 1/00* | (2006.01) |
| *B01D 53/85* | (2006.01) |
| *A01K 61/40* | (2017.01) |
| *A01K 61/50* | (2017.01) |
| *A01K 61/10* | (2017.01) |
| *A23K 10/12* | (2016.01) |

(Continued)

(52) U.S. Cl.
CPC ............. *A23K 50/30* (2016.05); *A01K 61/10* (2017.01); *A01K 61/40* (2017.01); *A01K 61/50* (2017.01); *A01K 67/02* (2013.01); *A01K 67/033* (2013.01); *A23K 10/12* (2016.05); *A23K 50/10* (2016.05); *A23K 50/70* (2016.05); *A23K 50/80* (2016.05); *A23K 50/90* (2016.05); *B01D 53/85* (2013.01); *C12M 29/02* (2013.01)

(58) Field of Classification Search
CPC .... B01D 53/84; B01D 2251/95; C12M 21/02; C12M 25/02; C12M 29/02; Y02C 10/02
See application file for complete search history.

(56) References Cited

U.S. PATENT DOCUMENTS

| | | | | |
|---|---|---|---|---|
| 4,806,148 A | * | 2/1989 | Ottengraf | B01D 53/84 435/299.1 |
| 8,569,050 B1 | * | 10/2013 | Ericsson | C12N 1/12 435/292.1 |

(Continued)

*Primary Examiner* — Michael L Hobbs
(74) *Attorney, Agent, or Firm* — The Webb Law Firm

(57) ABSTRACT

A process includes microbially degrading harvested polyculture plant material to form a concentrated microbial biomass and providing the concentrated microbial biomass to an intermediary animal for consumption. The process may also be directed to producing a product animal which includes providing a growth area having an outlet for waste and providing a harvested plant material collection area having an outlet for degradation products. The process may also include providing a microbial growth system for producing a bacterial biomass and directing at least some waste from the outlet of the product animal growth area to the harvested plant material collection area. The process may also include directing at least some degradation products to the microbial growth system, directing some of the microbial biomass produced in the microbial growth system to an intermediary animal for consumption, and directing the intermediary animal to a product animal growth area.

15 Claims, 22 Drawing Sheets

Related U.S. Application Data

(60) Provisional application No. 61/308,074, filed on Feb. 25, 2010.

(51) Int. Cl.
*A23K 50/10* (2016.01)
*A23K 50/70* (2016.01)
*A23K 50/90* (2016.01)
*A23K 50/80* (2016.01)
*A01K 67/02* (2006.01)
*A01K 67/033* (2006.01)

(56) References Cited

U.S. PATENT DOCUMENTS 9,681,644 B2 *  6/2017  Northrop ................ A01K 67/02
2005/0272146 A1 * 12/2005  Hodge ................ B01F 13/0827
                                                                435/289.1

* cited by examiner

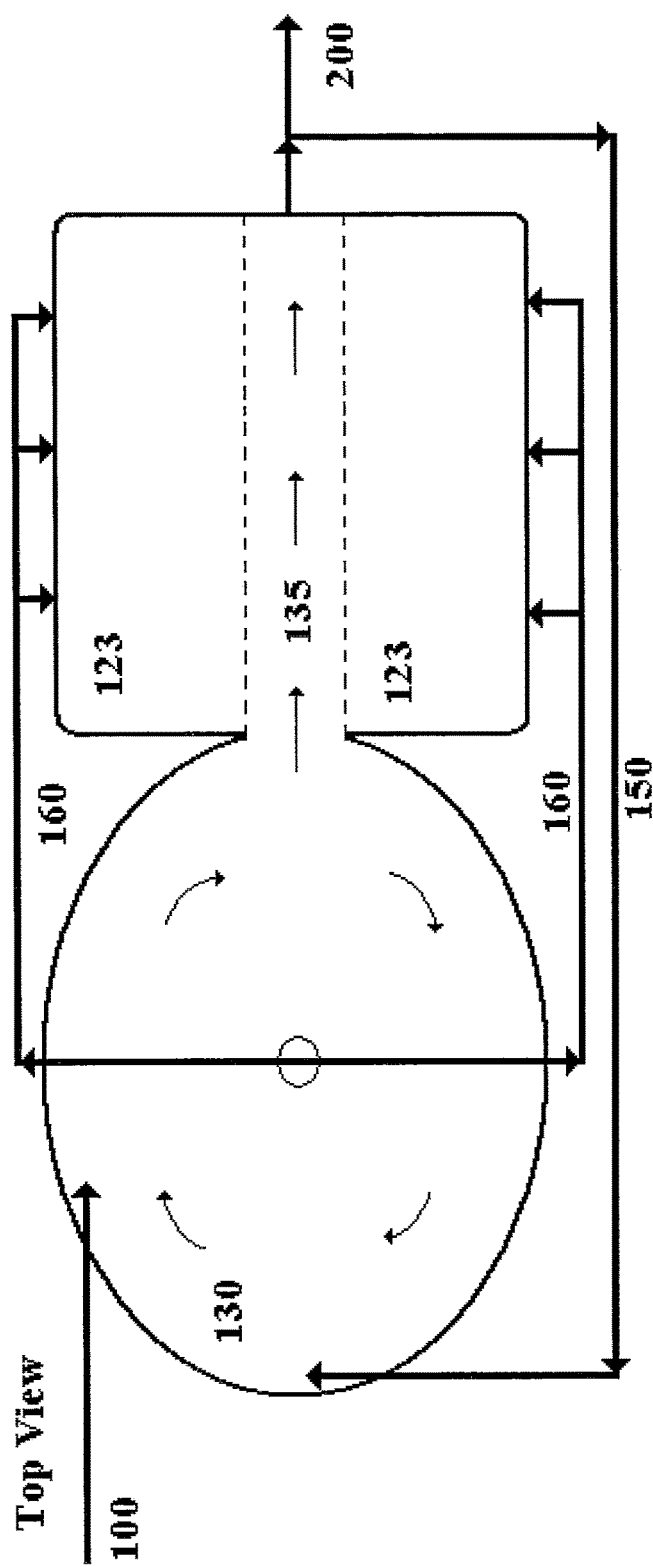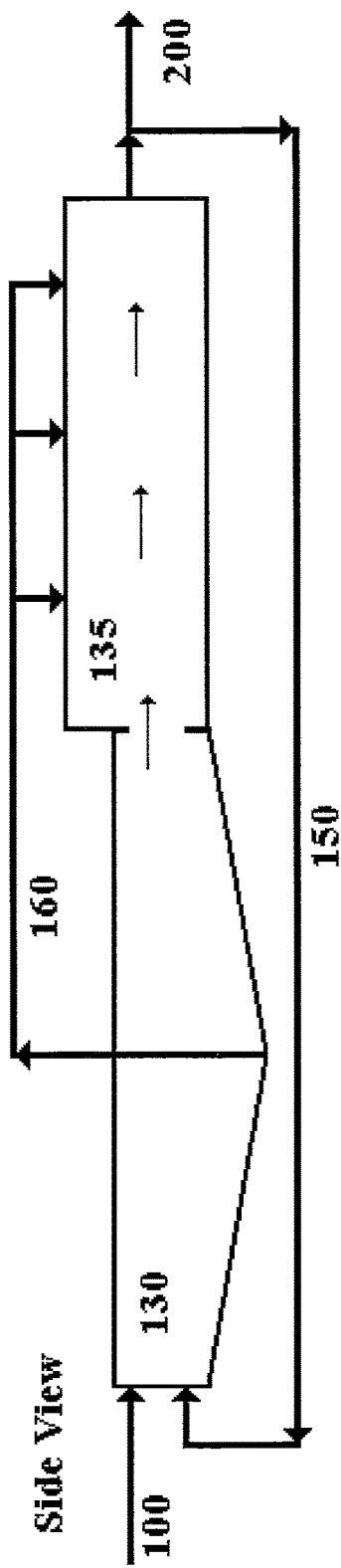
Figure 9a
Figure 9b

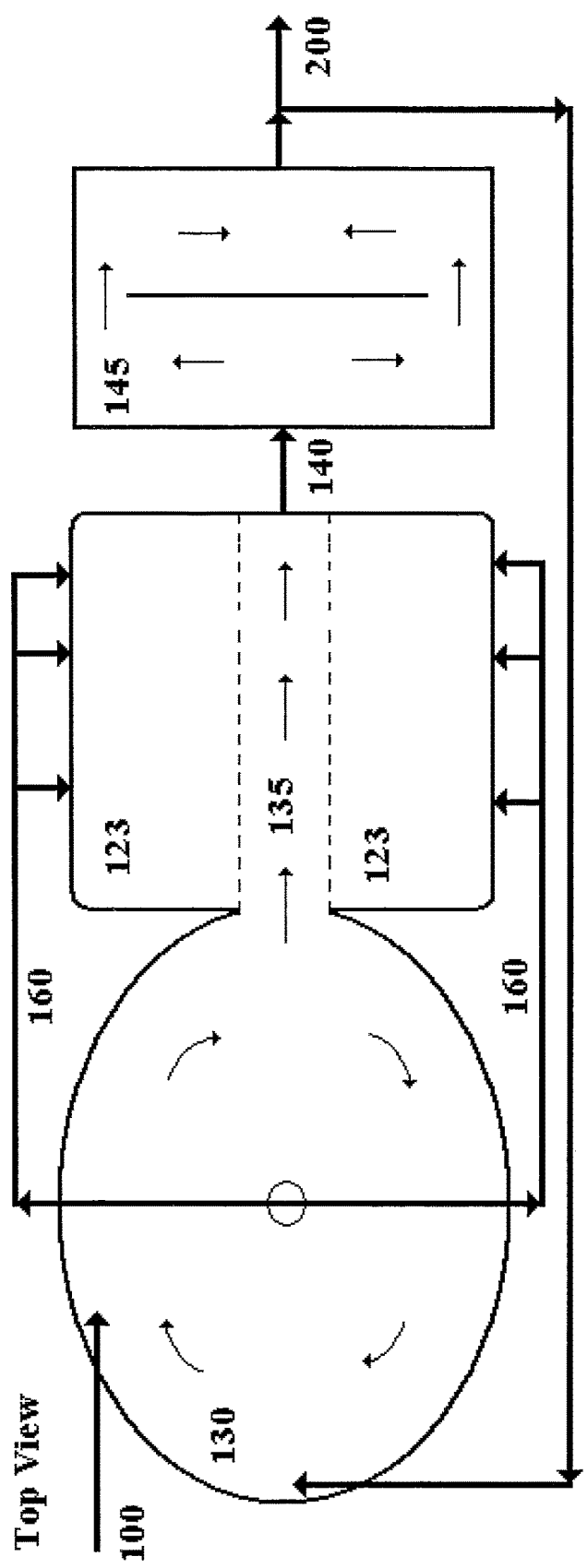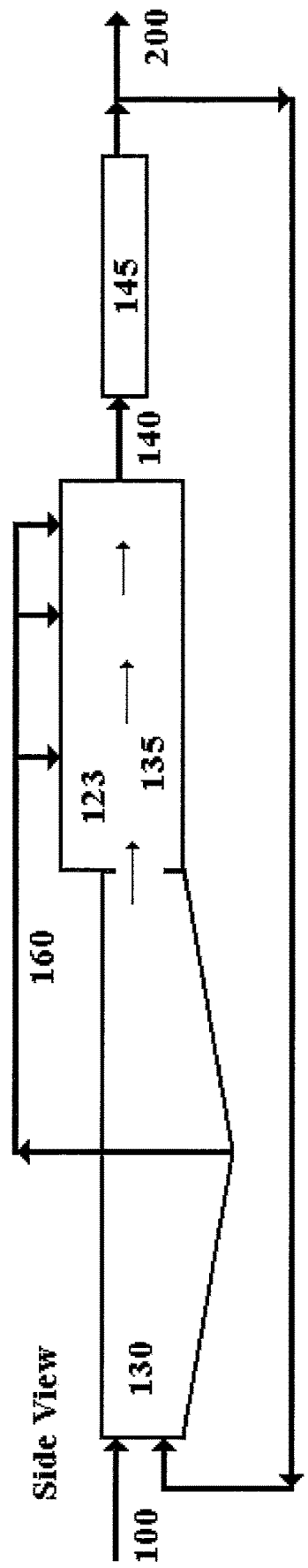
Figure 10a
Figure 10b

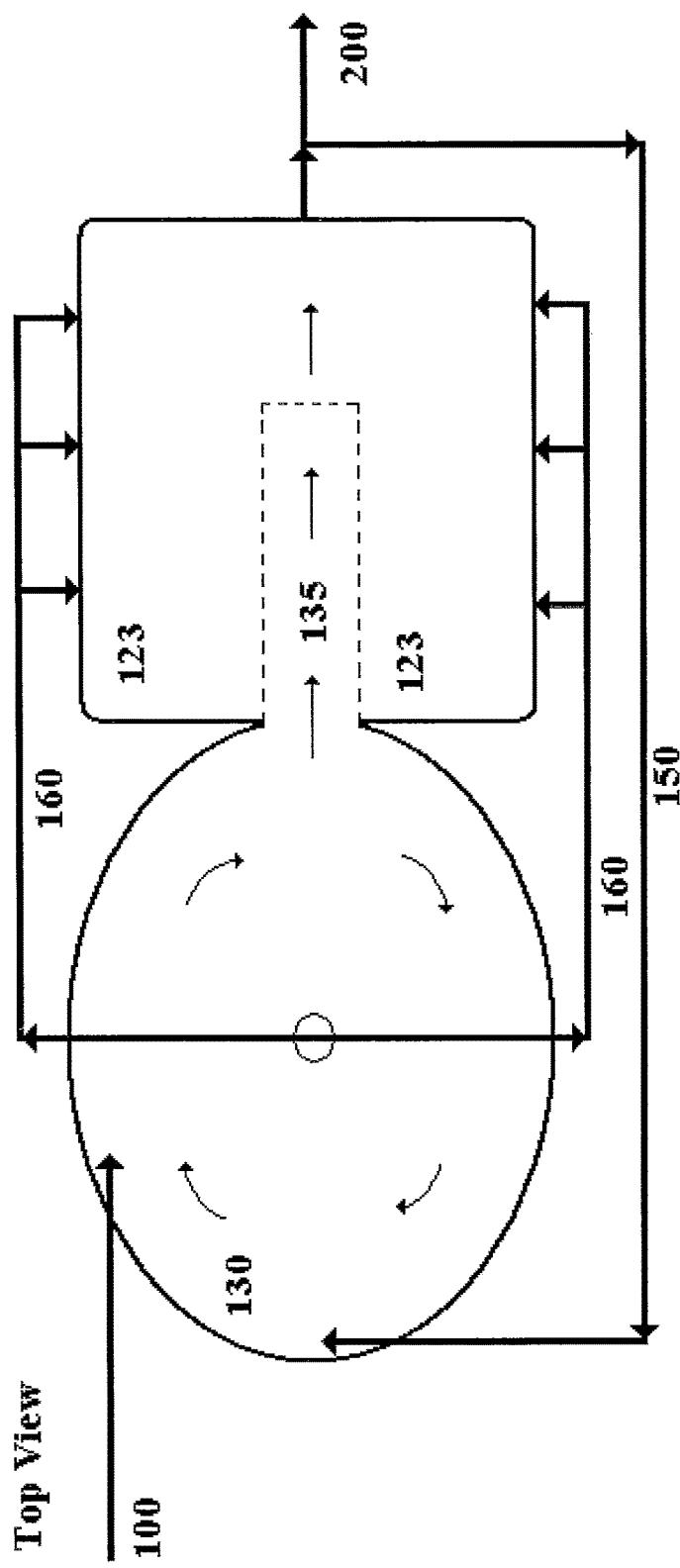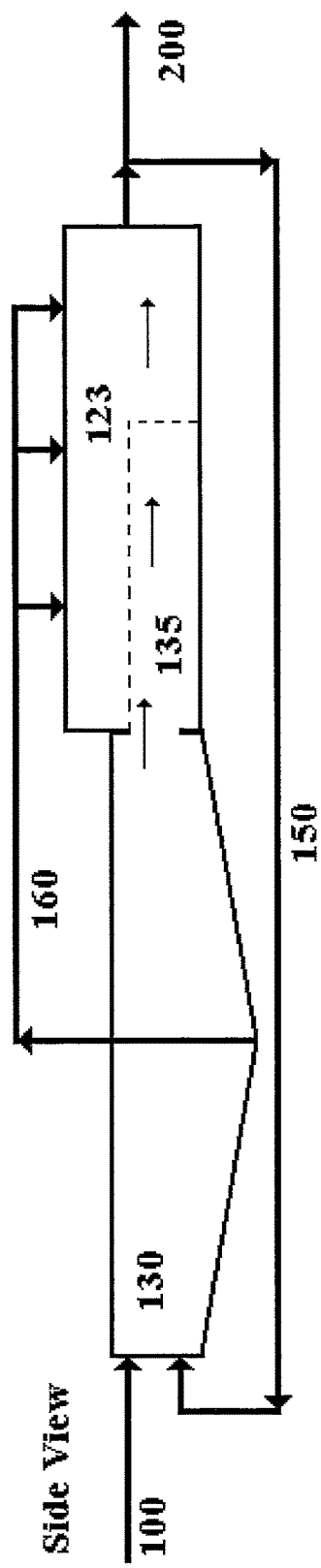
Figure 11a
Figure 11b

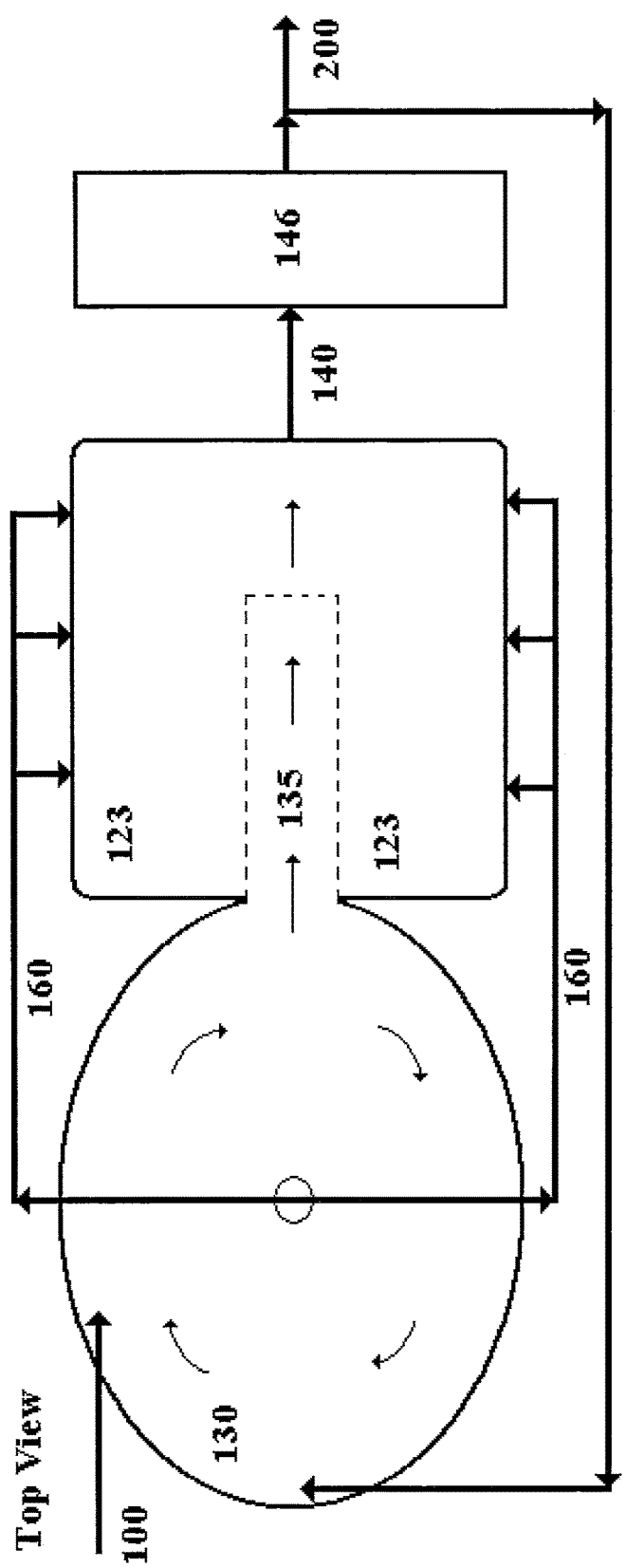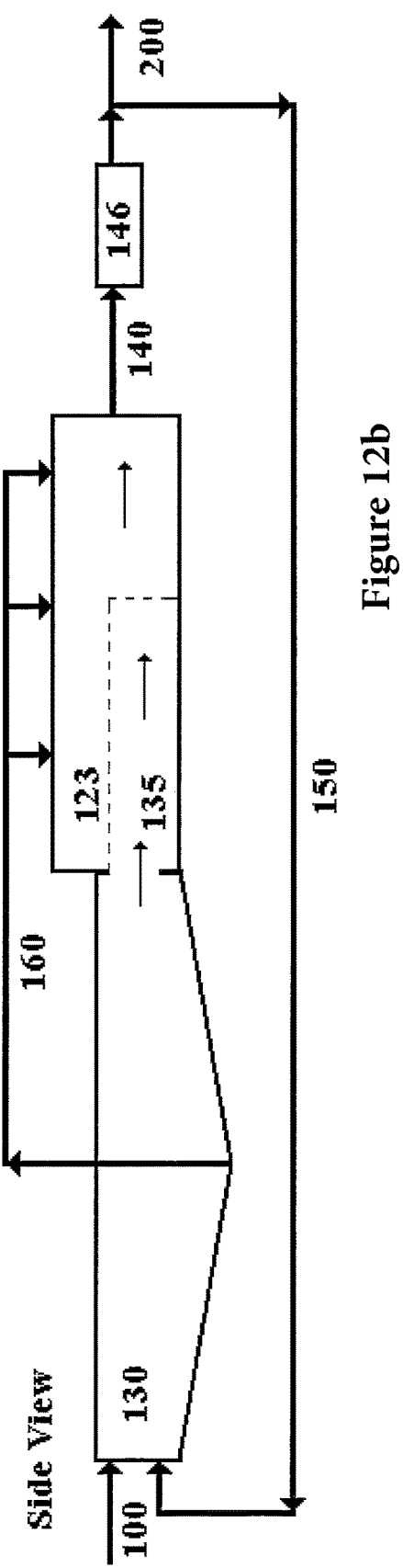
Figure 12a
Figure 12b

PROCESS AND METHOD FOR OPTIMIZING PRODUCTION OF FOOD AND FEED

CROSS REFERENCE TO RELATED APPLICATIONS

The present application is a continuation of U.S. application Ser. No. 13/580,299, now U.S. Pat. No. 9,681,644, filed Oct. 25, 2012, entitled "Process and Method for Optimizing Production of Food and Feed", which is a U.S. national stage application of International Patent Application No. PCT/US2011/026266, filed Feb. 25, 2011, entitled "Process and Method for Optimizing Production of Food and Feed", which claims priority to U.S. Provisional Application No. 61/308,074, filed Feb. 25, 2010, entitled "System and Method for Optimizing Production of Food and Feed", the entire disclosures of each of which are hereby incorporated by reference in their entirety.

BACKGROUND OF THE INVENTION

Field of the Invention

The present invention relates to a process for optimizing the production of food and/or feed by generating a concentrated microbial biomass from the degradation of harvested plant material obtained from a monoculture or polyculture plant community, and providing the concentrated microbial biomass for consumption by an intermediary animal.

Description of the Related Art

Over the last 10,000 years, but most significantly in the last 100 years, a series of agricultural practices have been developed for the production of food for consumption by humans. These practices have culminated in today's modern agriculture in which a variety of plants and animals are grown and harvested for food. Modern agriculture usually includes the cultivation of land; selection, planting, and growing of selected single species of plants; irrigation of fields with groundwater from aquifers and surface waters; suppression of other plants that might compete with the selected plants by applying chemicals such as herbicides; suppression and control of various diseases and pests which attack the selected plants by applying chemicals; and the stimulation and promotion of growth and health of the selected plants by applying fertilizers to the fields.

Modern animal production practices usually include raising animals such as cattle, sheep, and goats for meat and/or milk by; grazing on rangelands including pastures, grasslands, and prairies which may be natural or may be planted or seeded with one or more of a variety of desirable plants, such as feed crops; or by feeding the animals grains and other plant products which are produced utilizing one or more of the previously listed modern agriculture practices.

While this modern agriculture has allowed for an unprecedented rise in the world's population, it has also resulted in serious environmental pollution and degradation. In the last 150 years, over half of the world's forests and wetlands have been destroyed so that the land could be used for grazing animals or cultivated for agricultural plant production. Much of the carbon which had been sequestered in the destroyed forests and wetlands has now been released to the atmosphere as carbon dioxide where many believe it contributes to global climate change and global warming.

The modern agricultural practices have also led to the pollution of ground and surface waters with nutrients, pesticides, and other chemicals. This reduces and threatens fish populations as well as drinking water supplies. Raising large numbers of animals through conventional techniques also releases significant quantities of greenhouse gases to the atmosphere where again many believe that these gases contribute to global climate change. Another practice of modern animal agriculture concentrates large numbers of animals in confined spaces. This results in the production of large quantities of animal wastes containing nutrients and other materials which in large concentrations further pollute the environment The continual plowing and cultivation of the land and the widespread use of an increasing variety of pesticides has destroyed a large fraction of the topsoil that once existed. Modern practices also require excessive irrigation, which both depletes aquifers and increases the salinization of soils. As the organic fraction of the soil has been oxidized it has also been exposed to erosion, which not only depletes the soil but also leads to additional pollution of the groundwaters, lakes, streams, rivers, and even the oceans. A further consequence of this pollution has been the reduction of desirable fish populations in the waters of the earth. Eutrification and decline in water quality, destruction of spawning and nursery habitat, and continual overfishing have depleted many of the populations of the most desirable fish used for human food.

Accordingly, the present invention has been developed in view of inefficiencies, shortcomings and other disadvantages of conventional production practices.

SUMMARY OF THE INVENTION

The present invention includes a method of agricultural production in which diverse mixed plant communities are grown, maintained, and partially harvested in a periodic manner so that significant quantities of carbon are sequestered within the persisting plant communities. The periodically harvested plant material is collected and concentrated in a physically defined space. There it is microbially broken down, converted into a microbial biomass which is processed into food for human consumption or animal feeds, or is fed to one or more varieties of small intermediary animals which are in turn used directly for food, used as an animal feed, or used as a raw material for the production of processed foods and animal feeds. The animal excreta or unused byproducts of each stage of production may be recycled back to prior stages where they are used as inputs of nutrients and biodegradable raw materials. Water may also be recycled within the system and parts of the microbial growth systems and production lands can serve a water purification and filtration function.

The system of the present invention can use any material (Plant Material) produced by a photosynthetic reaction in plants. Generally the Harvested Plant Material will include Plant Material grown in forests or woodlots and will include whole trees and bushes, logs, branches, leaves, and roots. Plant Material may also include grasses, reeds, aquatic plants, shrubs, bushes, yard wastes, and a variety of agricultural products and byproducts such as corn stover, straw, hay, vegetable and fruit processing waste, etc. Plant Material may also include various produced or manufactured materials and products such as lumber, paper, cardboard, fabric, and the like.

In the process of the invention, the Plant Material is collected in a container, pond, tank, or the like, or is piled or placed on a pad or in a contained area where liquid emanating from the material can be collected. The Plant Material is then subjected to a microbial treatment process in which various constituents of the Plant Material are converted into a microbial cell mass or oxidized. The constituents most generally converted in this manner usually include cytoplasmic sap comprising proteins, nucleic acids, fats, oils, sugars and other molecular components of the plant cells, and the more easily digested fraction of the structural components of the Plant Material such as cellulose or parts of the hemicellulose fraction of the Plant Material.

Usually the fraction of the Plant Material which is converted into a microbial biomass is about 40 to 60% of the total mass. However, in some applications, as little as 5 to 10% or as much as 95% of the Plant Material may be converted.

During the bioconversion process, the Plant Material is usually submerged in water, either continuously or periodically. In other embodiments of the invention, the Plant Material may be stacked or placed either above water or on a pad or other impervious surface and occasionally sprayed or irrigated with water. Nutrients or fertilizers comprising sources of nitrogen, phosphorus, potassium, and other elements necessary for microbial growth may be introduced into the water or otherwise applied to the Plant Material to facilitate the growth of the microorganisms.

As a part of the bioconversion process microbes and part of the microbial biomass may be continually or intermittently removed from the Plant Material. This may involve physical separation techniques such as washing, rinsing, irrigating, hosing or other methods involving water or other aqueous solutions. It also could involve other physical methods which could remove small particles of degraded material which have microbes attached to their surfaces or embedded within the small particles. These physical methods of separation could involve blowing air on the material or shaking or otherwise mechanically disturbing the material to loosen and remove microbe containing small particles.

Other methods of continually or intermittently removing microbes from the Plant Material may involve the use of other biological organisms such as small fish, insects, snails, worms, or other macroinvertebrates. These organisms may have continuous or intermittent access to the Plant Material during which time they may collect or consume the microbes. The organisms may be separated from the collected Plant Material or they may be periodically harvested from within the collected Plant Material, either by various mechanical means, or through the use of other larger organisms such as larger fish, reptiles, amphibians, birds or mammals.

Once the microbial conversion and treatment process has progressed to a desired level of production of microbes, or destruction of the Plant Material, the remaining material (designated hereafter as the Biologically Processed Material) is collected and prepared for energy production. This preparation process may include rinsing, irrigating, hosing or other methods of cleaning the material to remove residual microbes and other collecting organisms.

The resulting Biologically Processed Material will comprise a different distribution of component compounds than will the Plant Material from which it was produced. Thus the Biologically Processed Material will contain relatively fewer nutrients, proteins, nucleic acids, sugars, starches, fats, oils, and other readily degradable substances than the original Plant Material. The Biologically Processed Material will also contain relatively less cellulose and hemicellulose, and relatively more lignin, than will the source Plant Material.

In one embodiment, Biologically Processed Material produced from the system of the present invention could produce fewer greenhouse gases if burned or incinerated than original or "raw" Plant Material. This may occur because nutrients such as nitrogen and sulfur would have been consumed by the biological treatment process and removed with the microbial biomass.

Once the Biologically Processed Material has been produced it is then further processed into an appropriate substrate for energy production. The further processing will usually entail drying and often will involve a mechanical process to convert the Biologically Processed Material into small particles. The mechanical process may involve grinding, shredding, chipping, chopping or other similar processes. The drying process may occur before, during, or after the mechanical process, or it may occur during some combination of these.

Once the Biologically Processed Material has been appropriately prepared physically and mechanically it becomes an Energy Substrate that can be used as a feedstock for an energy production process or a process which produces fuels or other energy products. The Energy Substrate may be used for straight incineration or combustion to provide heat to run a generator or fire a boiler. The Energy Substrate may also be used as a feedstock for a pyrolytic, gasification, or liquification process in which a variety of other usable energy products as well as heat may be produced. The useable energy products could include carbon, charcoal, alcohols, liquid oils, biodiesel, and burnable gases such as methane or a variety of mixtures of methane, hydrogen and carbon monoxide.

When the method of this invention is combined with a program of global reforestation and the steady state maintenance of existing and new diversified forests, it may result in a significant reduction in the concentrations of carbon dioxide and other greenhouse gases in the atmosphere. Other benefits of implementing the method of this invention with a global reforestation effort include the development of a microbial biomass which represents a new uncontaminated material which can be converted into a new food source capable of providing a high protein diet for all of the existing and projected population of the world. A significant reduction in the nutrient pollution of surface and ground waters may also be realized, in addition to preservation of biological biodiversity, biodynamic stability, and natural ecological habitat.

BRIEF DESCRIPTION OF THE DRAWINGS

FIG. 9a is a schematic representation of a top view of a combined system including a harvested plant material degradation system, a microbial growth system, and an intermediary animal system in the same physically confined space in accordance with an embodiment of the present invention;

FIG. 9b is a schematic representation of a side view of the combined system shown in FIG. 9a;

FIG. 10a is a schematic representation of a top view of a system including a plant growing system and water treatment system in accordance with an embodiment of the present invention;

FIG. 10b is a schematic representation of a side view of the system shown in FIG. 10a;

FIG. 11a is a schematic representation of a top view of a system including a fish access zone in accordance with an embodiment of the present invention;

FIG. 11b is a schematic representation of a side view of the system shown in FIG. 11a;

FIG. 12a is a schematic representation of a top view of a system including additional waste treatment systems in accordance with an embodiment of the present invention;

FIG. 12b is a schematic representation of a side view of the system shown in FIG. 12a.

DETAILED DESCRIPTION OF THE INVENTION

Figure 1:
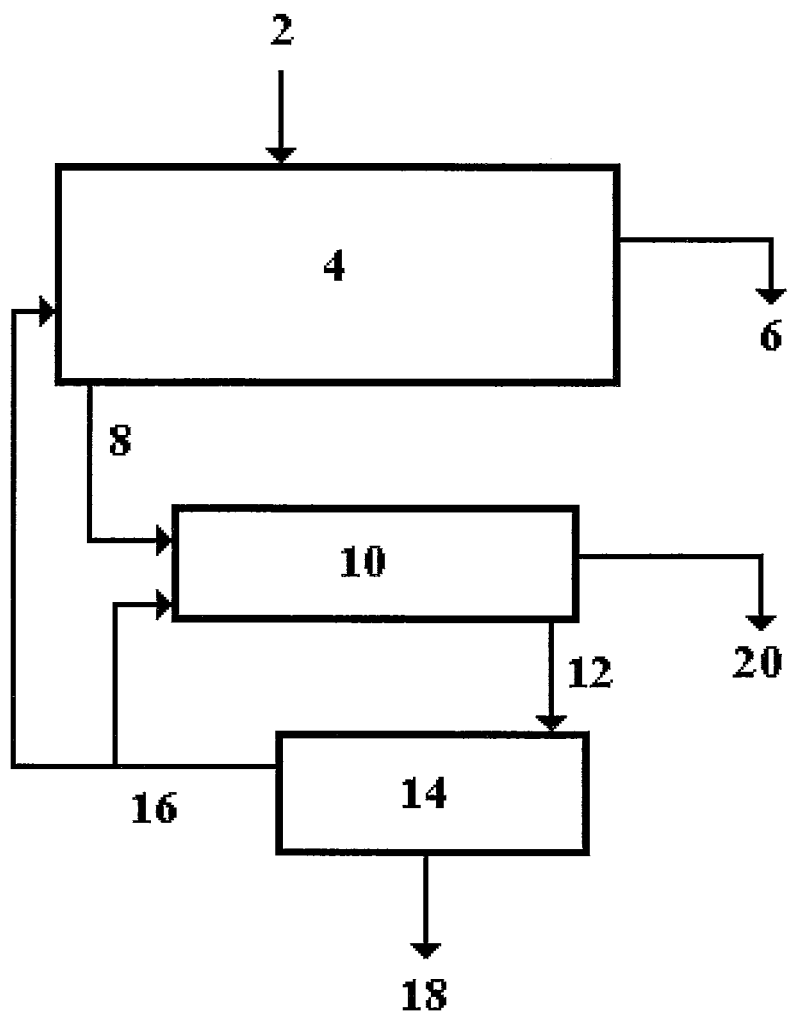
FIG. 1 is a schematic representation of a system in accordance with an embodiment of the present invention.

As shown in FIG. 1, harvested plant material 2 including material grown in terrestrial, wetland, or aquatic environments and byproducts produced from such material is loaded into a Harvested Plant Material Degradation (HPMD) System 4. As used herein, the term "harvested plant material" means material produced by a photosynthetic process which has been collected from the area where it was grown or concentrated in a part of the area where it was grown. The harvested plant material can be produced in a photosynthetic production system in which plant materials, including celluloses, lignins and/or starches, are produced via the process of photosynthesis on and/or in fields, grasslands, forests, wetlands, gardens, agricultural production lands, residential areas, suburban areas, and/or and aquatic systems. In one embodiment, the aquatic systems can include oceans, lakes, ponds, rivers, streams, and/or man made structures including lagoons, tanks, and containment structures. In one embodiment harvested plant material can include leaves, brush, trees, grass clippings, weeds, sawdust, organic food processing wastes, grasses, sedges, algae, aquatic plants, and/or agricultural residues. The plant communities from which the harvested plant material is obtained can comprise a polyculture of photosynthetic plants including a plurality of species of plants. The polyculture of plants can be a mixed and diverse community of plants, which grow in environments that are not plowed, mechanically cultivated, or contacted with pesticides and/or fertilizers. These can include plant communities growing in wetlands or aqueous environments. In another embodiment, harvested plant material can include plant material taken from monocultures or plants grown in cultivated environments. In another embodiment, harvested plant material can include newspaper, cardboard, sawdust, food wastes, or any substrate that is biodegradable, and either contains no toxic components or contains toxic components at a sufficiently low concentration so that the final use of material produced by the process of the invention is not considered toxic or harmful to animals and/or humans.

Plant material can be periodically harvested from an environment and this can be performed at a time and in a manner that minimizes the disruption of wildlife that uses that environment. Seeds, nutrients, and water may be introduced into an environment to enhance the amount and quality of plant biomass produced. By harvesting plant material that originates from a plant polyculture growing in an environment, the erosion of topsoil can be reduced and the nutrient and pesticide pollution associated with non point source agricultural runoff can be significantly limited. Land producing a polyculture of plant material can be more agriculturally productive since cultivation is not required, therefore the terrain does not need to be substantially flat.

As used herein, the term "Harvested Plant Material Degradation System" or "HPMD System" means a system for receiving harvested plant material and at least partially degrading at least a portion of the harvested plant material. Referring again to FIG. 1, the HPMD System 4 may include a tank, lined pond, or a solid floored pad, such as made of concrete or other hard impermeable material. The harvested plant material itself may be mechanically processed by a chipper, shredder, grinder, cutter, or other such mechanical device. The resulting chips, sticks, dust, or other particles may then be placed in a net, crib, bat, or other containment system which allows water, microbes, small intermediary animals, or fish, or any combination of these to access the processed plant material. Such containment structures containing the processed or collected plant material may be placed within a tank, lined pond, or solid floored pad in such a manner as to facilitate the contact of the plant material with water, microbes, small intermediary animals, and fish or other larger animals.

The harvested plant material may be contacted with an aqueous based liquid, such as submerged in fresh or salt water, have water sprayed or irrigated over and/or through the material, or subjected to an alternating cycle of submergence and irrigation. Nutrients, unused byproducts and animal excreta from subsequent production components, and/or microbial inoculations may be added to the harvested plant material to encourage microbial action, which breaks down the physical structure of the harvested plant material. This involves the breaking of the plant cell walls, the releasing of the cytoplasmic contents, and/or the complete or partial biodegradation of the cellulose, hemicellulose, and/or lignin, which constitute the structural material of the plants. This degradation may occur in any combination of aerobic, micro aerobic, or anaerobic environments, in air, or in fresh or salt water. Organisms involved in this process may include, but are not limited to, bacteria, protozoa, fungi, and algae. In one embodiment, non-biodegradable residues 6 can be periodically removed from the system and land applied. The HPMD System 4 can also include a tank, lined cell, silo, bunker silo, concrete pad and/or area of shaped land to collect rainfall and/or leachate.

Referring yet again to FIG. 1, small particulate and soluble degradation products from the HPMD System 4 can be introduced via fluid contacting means 8 into a Microbial Growth System 10. The Microbial Growth System 10 microbially degrades the small particulate and soluble degradation products to produce a microbial biomass. As used herein, the term "microbially degrading" means biologically converting organic biodegradable material or material produced by a photosynthetic process into microbial cells. As used herein, the term "microbial biomass" means an organic mass including at least one of bacteria, microorganisms, protozoa, fungi and/or algae. In one embodiment, the microbial biomass may exist as single cells and/or as multicellular aggregates. The microbial biomass can form floc, readily settleable aggregates, zoogleal and/or filamentous masses. In one embodiment, the microbial biomass may be a concentrated microbial biomass produced by settling, centrifugation and/or filtration. In another embodiment, the microbial biomass can have a concentration of at least $10^8$ microbial cells per ml. Fluid contacting means can include conventional piping, and the like, which allow the small particulate and/or soluble degradation products from the HPMD System 4 to contact microorganisms in the Microbial Growth System 10. As used herein, the term "Microbial Growth System" means a system or process in which microorganisms consume all or part of a material substrate and produce additional microorganisms and degradation byproducts from the substrate. The Microbial Growth System 10 may include any non-toxic substrate and may employ fixed film or suspended growth systems operating in aerobic, anaerobic, anoxic conditions, or any combination of these and which may involve the recycling of solids or liquids. The Microbial Growth System 10 may include standard wastewater treatment technologies such as Activated Sludge, Sequencing Batch Reactor, Trickling Filters, Rotating Biological Contactors, Aerobic or Anaerobic Digestion, or the like. It also may include a bioreactor or chemostat type system as used in the fermentation, pharmaceutical, or other biotechnology industries.

In one embodiment, the Microbial Growth System 10 utilizes microbial growth to produce a harvestable microbial biomass, which may incorporate the microbes, metabolic byproducts, residues or other non-degraded components of the HPMD System 4. The inputs to the Microbial Growth System 10 may be soluble or particulate in nature and may also include additional nutrients and/or unused byproducts from subsequent production components. This system may employ fixed film or suspended growth systems with or without recycling of solids or liquids. The microbes may grow in aerobic, anaerobic, or anoxic conditions in fresh or salt water, and may include, but not be limited to, facultative microbes, bacteria, protozoa, fungi, and unicellular or small algae. This system also includes a means of concentrating and harvesting the produced microbial biomass. This may include the formation and settling of a floc, gravity settling, filtration, centrifugation, or other means of solids separation.

In one embodiment, solid residues from the Microbial Growth System 10 are periodically collected by a variety of conventional dewatering technologies such as gravity settling, filtration, presses, centrifuges, or the like. Excess water is discharged from the Microbial Growth System 10 as a liquid effluent 20.

In one embodiment an HPMD System 4 can directly produce a microbial biomass and this can occur with or without a means of concentrating said microbial biomass. In another embodiment a microbial growth system can act directly on a substrate which has not been previously acted on by an HPMD System 4. Generally such an embodiment is used in cases where the substrate has low concentrations of cellulose, hemicellulose, or lignin, or is a readily biodegradable material such as a food, food byproduct, or animal waste or wastewater.

Referring again to FIG. 1, the microbial biomass collected and produced by the Microbial Growth System 10 is delivered via 12, usually by pumping or gravity flow, to an Intermediary Animal System 14. As used herein, the term "Intermediary Animal System" means a system in which at least one variety of species is grown or maintained, which feed upon a microbial biomass produced by a microbial growth system. Intermediary animals can include small fish, such as any fish fry or minnows, worms such as annelids (including Oligochaetes), mollusks, including clams, snails, oysters, and mussels, arthropods, including insects and larvae, and/or crustaceans, including shrimp, crabs, lobster, and crayfish.

Any external source of a microbial biomass could be used as the feed stream for the Intermediary Animal System 14 provided that sufficiently low concentrations of toxic constituents are present. Thus residues from wine or beer fermentations, sludges from conventional wastewater treatment plants, biomass residuals from manure management systems, etc. could be used as Intermediary Animal System 14 input sources.

In one embodiment, animal excreta from the intermediary animals can be recycled back to the Microbial Growth System 10 or the HPMD System 4. Animal excreta and/or unconsumed microbial biomass from the Intermediary Animal System 14 can be discharged along with any excess water as a subsystem effluent 16 which is recycled back to other production systems such as the HPMD System 4 or Microbial Growth System 10. Harvested intermediary animals 18 are periodically removed from the Intermediary Animal System 14. In one embodiment the intermediary animals are harvested by mechanically separating the intermediary animals from the system. In another embodiment, the intermediary animals are removed from the system by draining the tank or containment area, gravity settling, hooking, netting, filtering and/or other conventional mechanical separation procedures. In another embodiment, the intermediary animals may self harvest themselves by crawling, swimming, or otherwise moving themselves out of the Intermediary Animal System 14.

Figure 2:
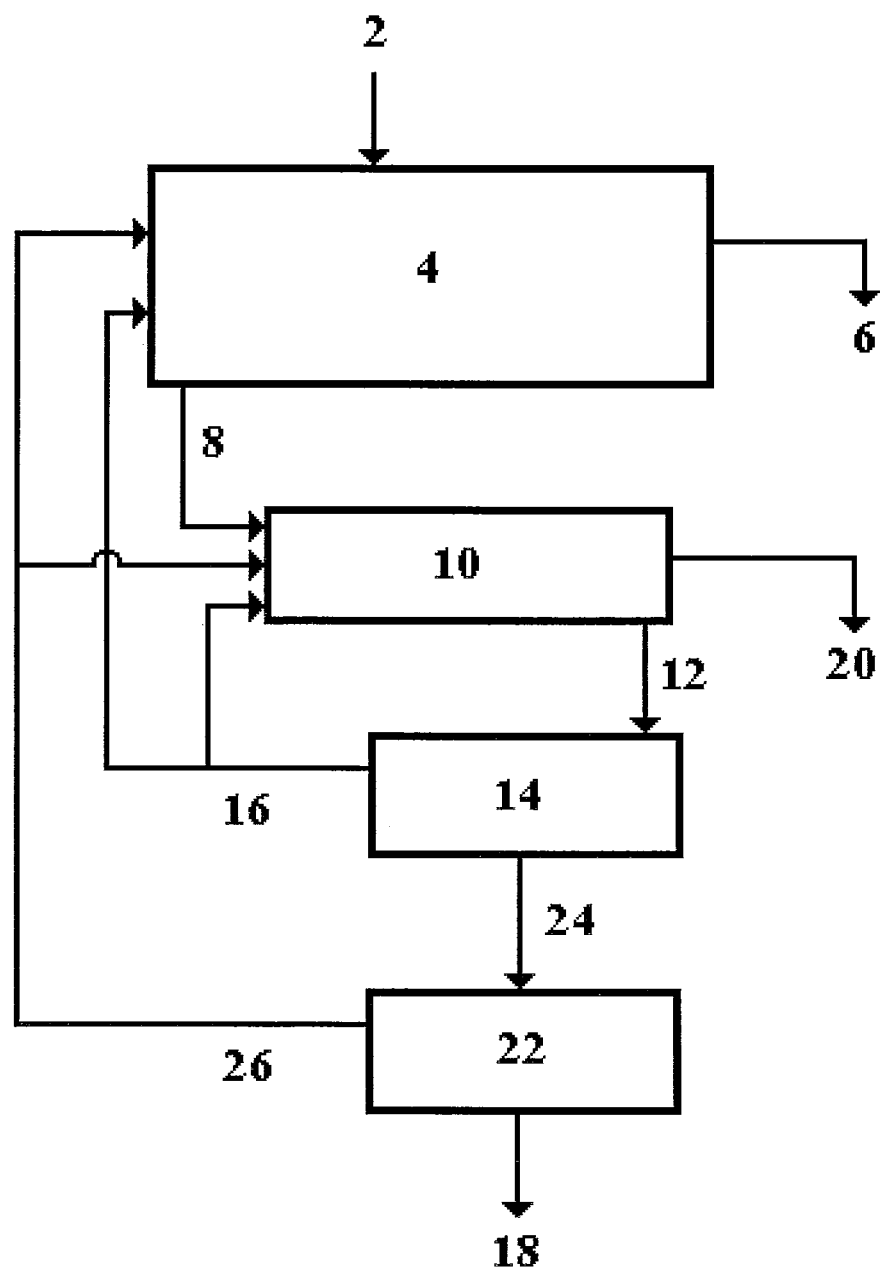
FIG. 2 is a schematic representation of a system including a harvested plant material degradation system, a microbial growth system, and an intermediary animal system combined with a processing system in accordance with an embodiment of the present invention.

In another embodiment as shown in FIG. 2, the HPMD System 4, the Microbial Growth System 10 and the Intermediary Animal System 14 are combined with a Processing System 22. Here the harvested intermediary animals are transferred from the Intermediary Animal System 14 via 24 to the Processing System 22 where they are converted into animal feed, human food, or an edible substrate for processed foods 18 through conventional food processing techniques. In one embodiment, the intermediary animals can be processed into a fish food, such as a pelletized fish food, in the Processing System 22. Animal excreta, unused microbial biomass wastes from the Intermediary Animal System 14, and/or the unused byproducts from the Processing System 22 can be recycled via 26 to the Microbial Growth System 10 or the HPMD System 4 for reuse.

Figure 3:
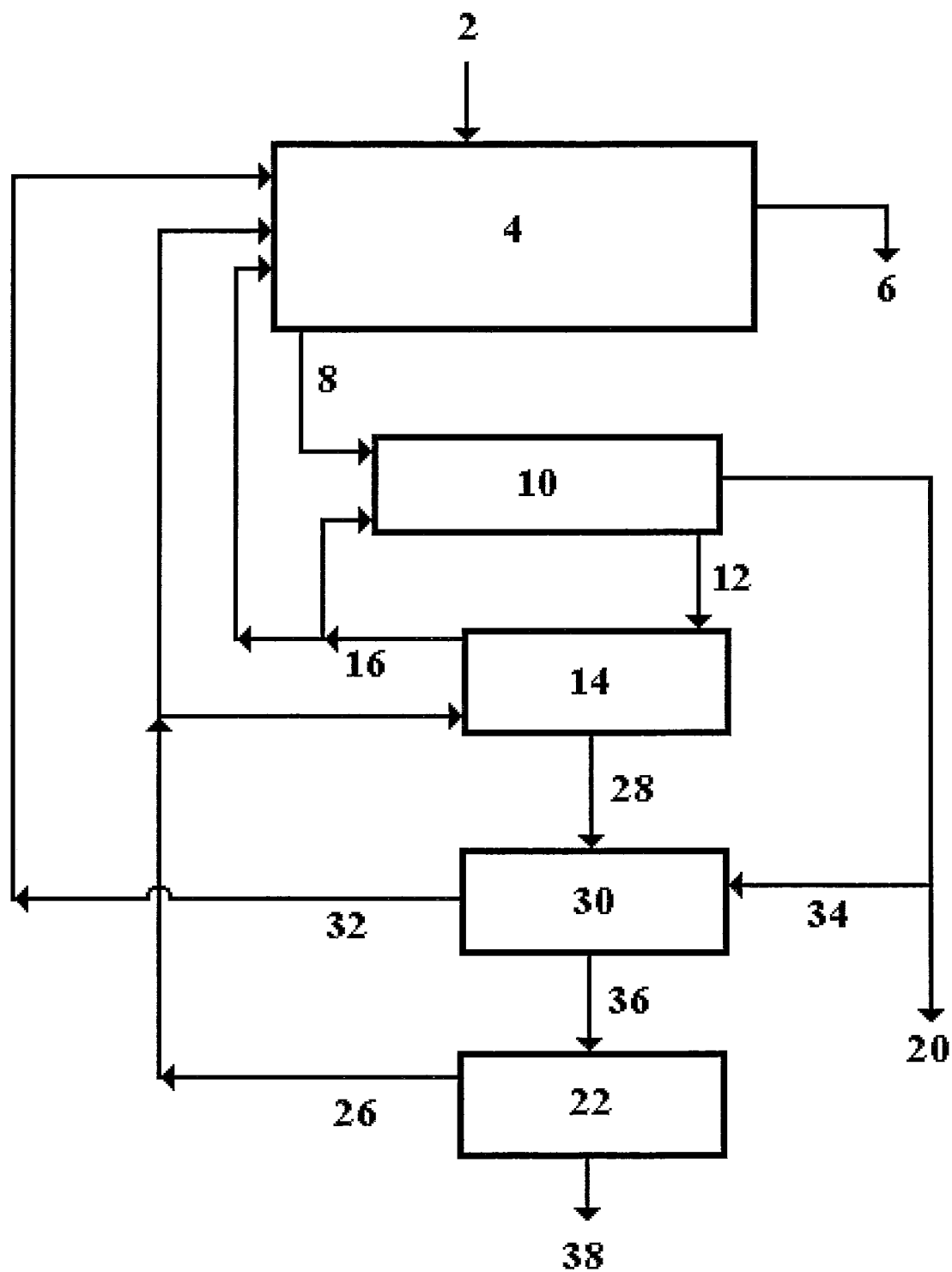
FIG. 3 is a schematic representation of a system including a fish growing system in accordance with an embodiment of the present invention.

In another embodiment as shown in FIG. 3, harvested plant materials and nutrients 2 are introduced to the HPMD System 4 which directs degradation products via 8 to the Microbial Growth System 10, which produces a microbial biomass. The microbial biomass is sent via 12 to feed the Intermediary Animal System 14 which in turn produces intermediary animals, such as aquatic worms or oligochates, insect larvae, and/or crayfish. The intermediary animals are then provided via 28 to feed a product animal, such as a crustacean, mollusk, fish, pig, goat or cow, or other animal typically consumed by humans, in a Product Animal System 30. In one embodiment, the Product Animal System 30 is a fish growing system.

The fish growing system can produce fish that consume the animals grown in the Intermediary Animal System 14 as part or all of their diet. Feed other than the intermediary animal may be used to supplement the diet of the fish. In one embodiment, all or part of the effluent water from a tank housing product animals can be recycled back to the Microbial Growth System 10 or the HPMD System 4 via 32. In one embodiment, the recycled effluent can be taken from the bottom of a tank housing the fish in the fish growing system so that the solid excreta produced by the fish are removed. Clean water produced by the Microbial Growth System 10 can be used as influent water 34 for the Product Animal System 30 and excess water is discharged from the Microbial Growth System as effluent 20.

In one embodiment, fish can be sent via 36 to a Processing System 22 which produces cleaned fish and/or fish fillets 38. The unused byproducts from the Processing System 22 can be fed via 26 back to the Intermediary Animal System 14 and/or are recycled back to the HPMD System 4. Animal excreta, unused microbial biomass, and effluent from the Intermediary Animal System 14 are recycled via 16 back to the HPMD System 4 or the Microbial Growth System 10.

Figure 4:
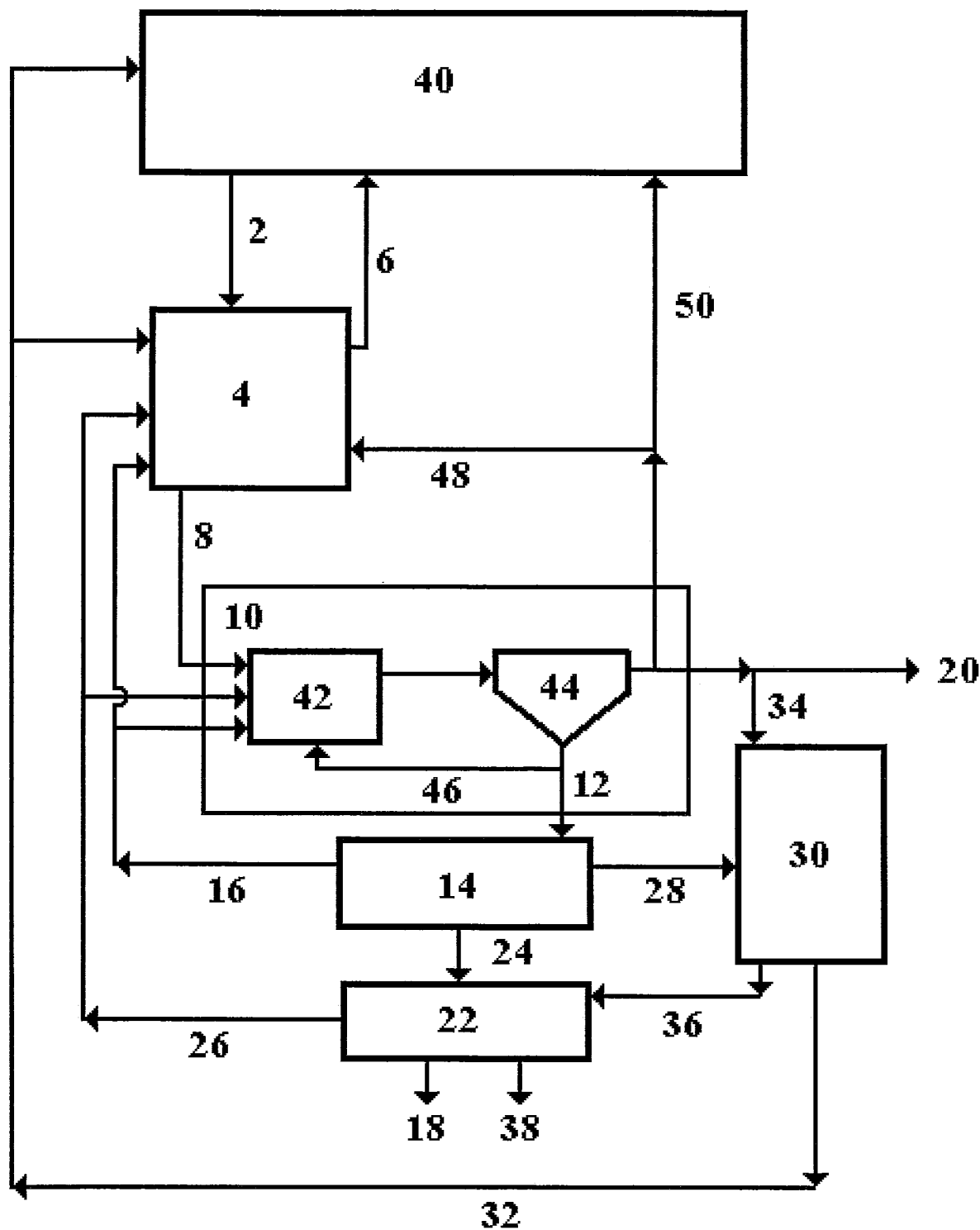
FIG. 4 is a schematic representation of a full scale production system in accordance with an embodiment of the present invention.

In yet another embodiment as shown in FIG. 4, a full scale production system of the invention includes an ecologically contained unit that operates on a given unit of land. As shown in FIG. 4, a Photosynthetic Production System 40 includes a forest, field, wetland, or body of water used to produce plant material. Harvested plant material can be collected at intermittent intervals, such as annually, from the Photosynthetic Production System 40. This harvested plant material will be transferred via 2 to an HPMD System 4. Nutrients can be added to optimize microbial growth. Non-biodegradable residues 6 may be periodically removed from the system and land applied to the Photosynthetic Production System 40.

As the harvested plant material is degraded the soluble and small particulate byproducts will be transferred via 8 to a Microbial Growth System 10 which may include an activated sludge type system including a bioreactor 42, clarifier 44, and recycle line 46. In one embodiment, the output from the HPMD System 4 may be further converted into microbial biomass which is embedded into a settleable floc structure. This settleable floc can then be substantially separated from the water in the clarifier 44 and the concentrated microbial biomass may be introduced via 12 into the Intermediary Animal System 14.

The effluent from the clarifier 44 may be used directly as a fresh water feed 34 to the Product Animal System 30, such as a fish raising tank if it has high enough water quality, or it may be diverted back via 48 to the HPMD System 4 or via 50 to the Photosynthetic Production System 40 for land application, or discharged as a final effluent 20.

In one embodiment, the concentrated microbial biomass, such as having about 2% solids, may be fed via 12 into large shallow trays or other structures in the Intermediary Animal System 14 where environments conducive to the rapid growth of a series of intermediary animals have been constructed. The intermediary animals, such as crayfish, aquatic worms, oligochaetes, clams, snails, scuds, insect larvae, minnows, and the like may eat the microbial biomass directly. In one embodiment, the intermediary animals can be frequently harvested to maintain optimal population densities for maximum consumption of the microbial biomass and production of the intermediary animals. Animal excreta and unused microbial biomass from the Intermediary Animal System 14 may be returned via 16 back into the HPMD System 4. The harvested intermediary animals may be fed via 28 to the animals in the Product Animal System 30, such as fish in a fish tank, or may be sent via 24 to a Processing System 22.

If the various systems so far described produce something other than a whole product animal, then a Processing System 22 may be included to convert the intermediary animals into a product that is typically consumed by humans. For example, fish, crayfish, clams, snails and the like may require cleaning and processing prior to sale for human consumption. In one embodiment, a Processing System 22 can include a fish cleaning and/or filleting operation. Here the final product would be the cleaned fish or the fish fillets. The unused byproducts produced of this processing operation may be returned back to the Microbial Growth System 10 or the Intermediary Animal System 30. In one embodiment, fish cleaning residues such as guts, heads, fins, bones, and the like can be fed to crayfish in the Intermediary Animal System 30. In a more elaborate form, the Processing System 22 may include a system for converting intermediary animals into a synthetic food. In another embodiment, the Processing System 22 may convert intermediary animals into a pelletized food for feeding to fish.

Referring again to FIG. 4, animal excreta, unused microbial biomass, and effluent from the Intermediary Animal System 30 can also be recycled via 26 back to the HPMD System 4 or the Microbial Growth System 10. Wastes and effluent from the Product Animal System 30 may be recycled via 32 back to the HPMD System 4 or the Photosynthetic Production System 40.

Figure 5:
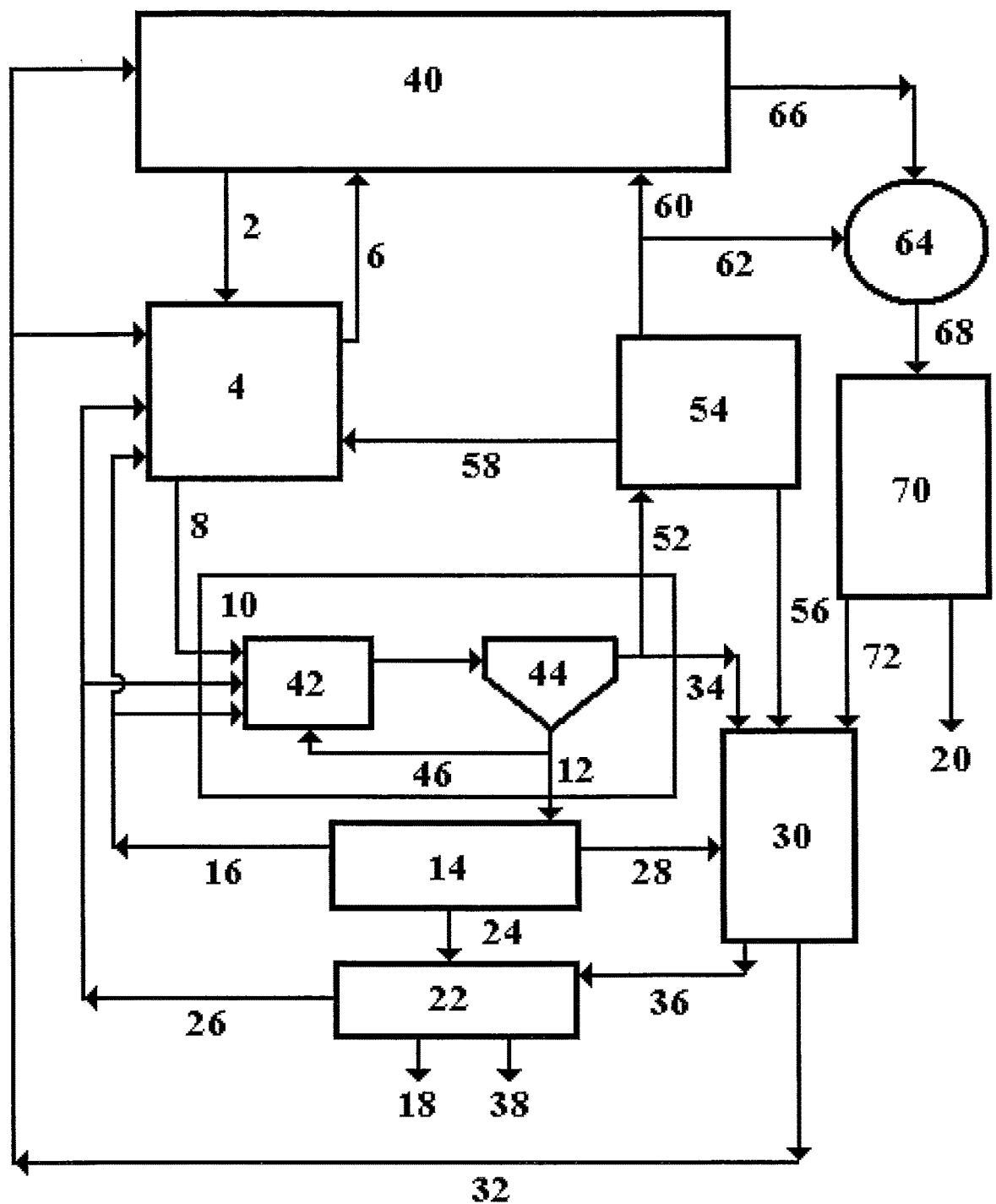
FIG. 5 is a schematic representation of a system including additional water retention and final effluent polishing features in accordance with an embodiment of the present invention.

In yet another embodiment as shown in FIG. 5, a full scale production system of the present invention can include an ecologically contained unit that operates on a given unit of land with additional water retention and final effluent polishing features. In one embodiment, a Photosynthetic Production System 40 includes a forest, field, wetland, or body of water used to produce plant material. Harvested plant material may be collected intermittently or once a year from the Photosynthetic Production System 40. This harvested plant material may be transferred via 2 to an HPDM System 4. In one embodiment, nutrients may be added to optimize microbial growth. As the harvested plant material is degraded, the soluble and small particulate byproducts may be transferred via 8 to a Microbial Growth System 10, which may include an activated sludge type system including a bioreactor 42, a clarifier 44, and separated solids recycle line 46. Here the output from the HPMD System 4 may be further converted into microbial biomass in 42 in the form of a settleable floc structure. The settleable floc structure can then be separated from the water in the clarifier 44 and the concentrated microbial biomass may be recycled back to the bioreactor 42 via the separated solids recycle line 46, or introduced via 12 into the Intermediary Animal System 14.

The effluent from the clarifier 44 can be used directly as a fresh water feed via 34 to a Product Animal System 30, such as a fish raising tank if it has high enough water quality, or it may be diverted via 52 through a sand filter or a wetland 54 and then via 56 to the Product Animal System 30. In one embodiment, the effluent from the clarifier 44 is introduced via 52 into a constructed wetland for the purposes of aeration, additional filtration and removal of suspended solids, and nutrient removal. This polished effluent then may be used via 56 as the influent water for the Product Animal System 30 or may be recycled back to the HPMD System 4. The effluent may also be land applied via 60 back to the Photosynthetic Production System 40 or sent via 62 to a collection pond 64. From there it may be transferred via 68 for further treatment in a constructed polishing wetland 70. Effluent from the polishing wetland 70 can be used as a fresh water feed 72 to the Product Animal System 30, such as a fish raising tank. Excess effluent can be discharged from the polishing wetland 70 as a final effluent 20.

The concentrated microbial biomass, such as having about 2 percent solids, may be fed via 12 to the Intermediary Animal System 14 and distributed into large shallow trays or other structures where environments conducive to the rapid growth of a series of intermediary animals have been constructed. The intermediary animals, such as crayfish, aquatic worms, oligochaetes, clams, snails, scuds, insect larvae, minnows, and the like may eat the microbial biomass directly. The intermediary animals may be frequently harvested to maintain optimal population densities for maximum consumption of the microbial biomass and production of the intermediary animals. Animal excreta and unused microbial biomass from the Intermediary Animal System 14 may be returned via 16 back into the HPMD System 4. The harvested intermediary animals may be fed via 28 to the animals in the Product Animal System 30, such as fish in a fish raising tank, or sent via 24 to a Processing System 22 which produces feed, food or processed food 18 from the intermediary animals.

In one embodiment, fish are sent via 36 to a Processing System 22 which produces cleaned fish and fish fillets 38. The unused byproducts from the Processing System 22 are recycled back via 26 to the HPMD System 4 or the Microbial Growth System 10. Animal excreta, unused microbial biomass, and effluent from the Intermediary Animal System 14 and the Product Animal System 22 are recycled back to the HPMD System 4 or the Photosynthetic Production System 40, as described earlier.

In another embodiment effluent from a fish raising tank may be returned via 32 to the HPMD System 4. In another embodiment, the effluent may also be diverted to the Photosynthetic Production System 40 depending on flow and water quality requirements for the desired fish to be raised. Runoff from the Photosynthetic Production System 40 may be collected via 66 in a holding area 64, such as a pond, and then transferred via 68 for further treatment in a constructed polishing wetland 70. Effluent from the polishing wetland 70 can be used as a fresh water feed 72 to the Product Animal System 30, such as a fish raising tank. Excess effluent can be discharged from the polishing wetland 70 as a final effluent 20.

Figure 6:
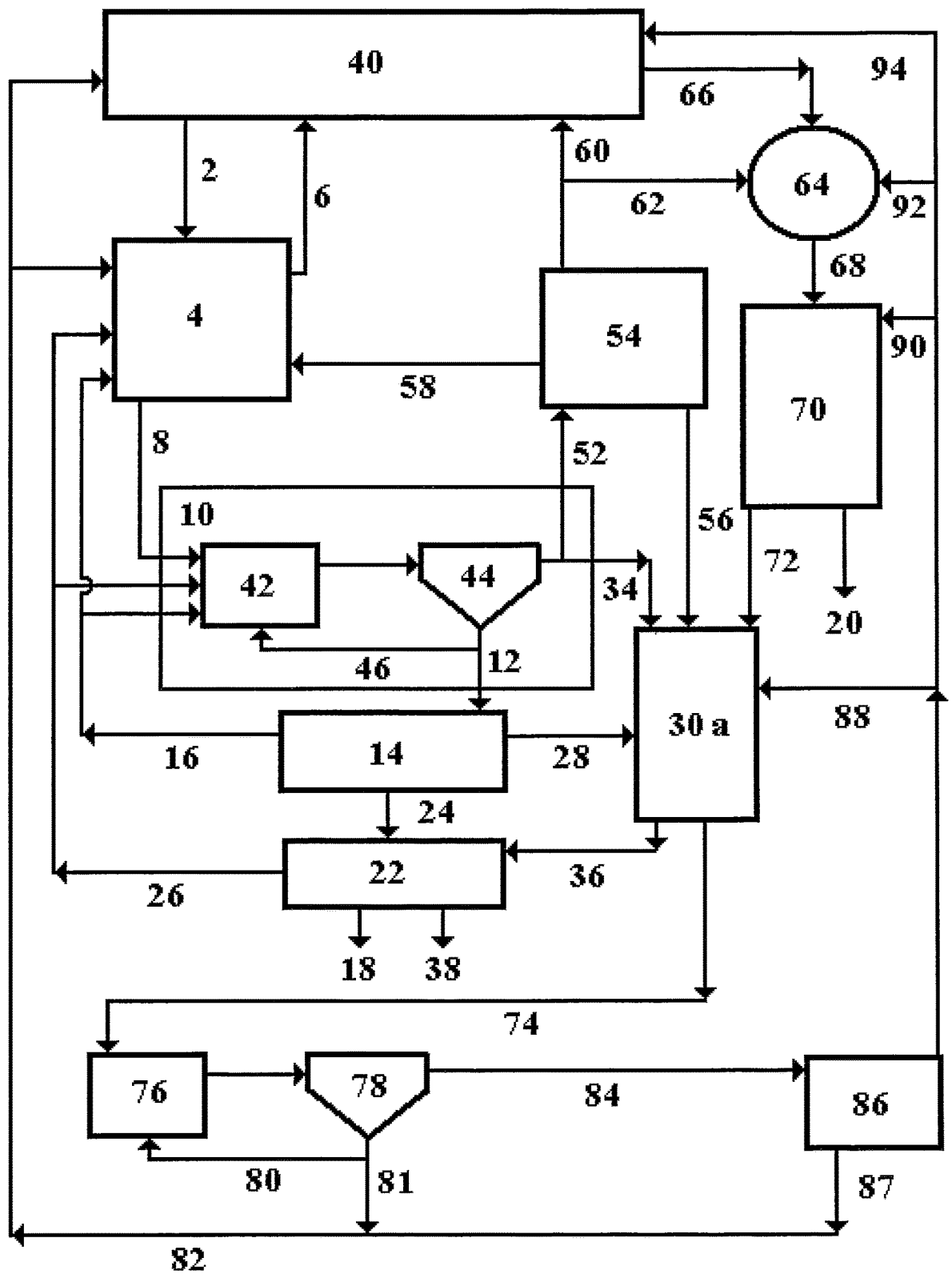
FIG. 6 is a schematic representation of a system including waste treatment of a fish production system in accordance with an embodiment of the present invention.

A further expansion on this system with additional water retention and treatment provisions is shown in FIG. 6. In this embodiment, the system described in FIG. 5 is expanded by including additional wastewater treatment of the Product Animal System 30, which in FIG. 6 shall be referred to with reference to a Fish System 30a. As shown in FIG. 6, the Fish System 30a effluent is transferred via 74 for further treatment with an activated sludge type water treatment system including a bioreactor 76 and clarifier 78 with a concentrated solids recycle loop 80. The Fish System 30a effluent can be microbially treated in the bioreactor 76 and then transferred via 77 to the clarifier 78 where the microbial solids are partially separated from the liquid. Clarifier 78 effluent may be transferred via 84 to a sand filter 86 for further effluent polishing. Waste solids 81 from the clarifier 78 and backwash 87 from the sand filter 86 can be recycled via 82 to the Plant Production System 40 or the HPMD System 4. The clean water effluent from the sand filter 86 can be recycled via 88 to the Fish System 30a, recycled via 92 to a collection pond 64, recycled via 90 to the polishing wetland 70, or recycled via 94 back to the Plant Production System 40 for land application. Excess water is discharged via 20 as final effluent from the polishing wetland 70.

In the various embodiments of the invention described herein, the HPMD System 4 and Microbial Growth System 10 may operate with total nitrogen concentrations, and in particular with ammonia and ammonium ion concentrations, which are sufficiently low such that the resulting concentrations of ammonia and ammonium ions in the Product Animal System 30 or the Fish System 30a do not interfere with the growth and health of the fish or other product animal. In an alternative embodiment the influent to and effluent from the Product Animal System 30 or the Fish System 30a is uncoupled from the HPMD System 4 and the Microbial Growth System 10, and an additional water treatment system is installed to maintain water quality in the Animal System 30 or the Fish System 30a.

The addition of the additional treatment system for the fish/animal wastes allows for much higher concentrations of nutrients, particularly various forms of nitrogen, to be maintained in the HPMD System 4 and the Microbial Growth System 10. This in turn may increase the rate of microbial conversion of harvested plant material to microbial biomass from that attainable in low nitrogen concentration systems.

Figure 7:
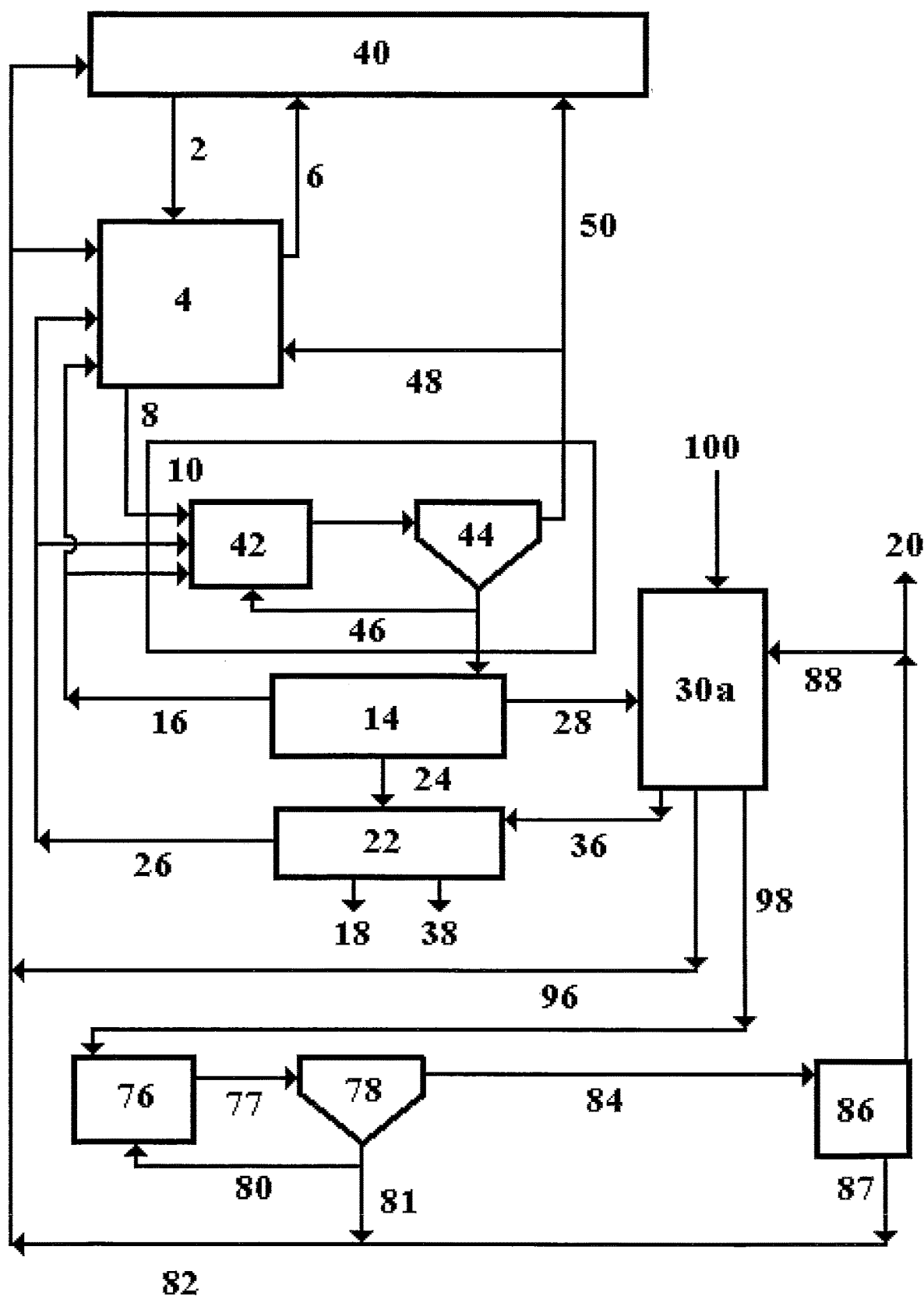
FIG. 7 is a schematic representation of a system including a bioreactor, clarifier, and sand filter in accordance with an embodiment of the present invention.

As shown in FIG. 7 the additional treatment system added to the system shown in FIG. 4 includes an activated sludge type system including a bioreactor 76 and a clarifier 78 followed by a sand filter 86. In this embodiment, fish wastes from the bottom of the Fish System 30a may be transferred via 96 to the Plant Production System 40 or the HPMD System 4. Effluent from the Fish System 30a may be transferred via 98 to the bioreactor 76 where soluble and small particulate fish wastes are microbially degraded and converted into biomass. The biomass may then be sent via 77 to the clarifier 78 where it is separated from the majority of the water stream. The collected solids are sent via 81 and/or 82 to the Plant Production System 40 or the HPMD System 4. The clarified water is sent via 84 for further treatment in the sand filter 86. Clean water from the sand filter 86 may be sent via 88 to the Fish System 30a or discharged as final effluent 20. Backwash wastes from the sand filter 86 can be sent via 87 and/or 82 to the Plant Production System 40 or the HPMD System 4. Similar wastewater treatment systems such as trickling filters, rotating biological contractors, various biological nutrient removal systems, suspended growth systems, fixed film systems and the like may be used in as partial or complete replacements for the above-described activated sludge type system. In this embodiment some clean external water 100 may be periodically added to the Fish System 30a to maintain overall water balance.

Figure 8:
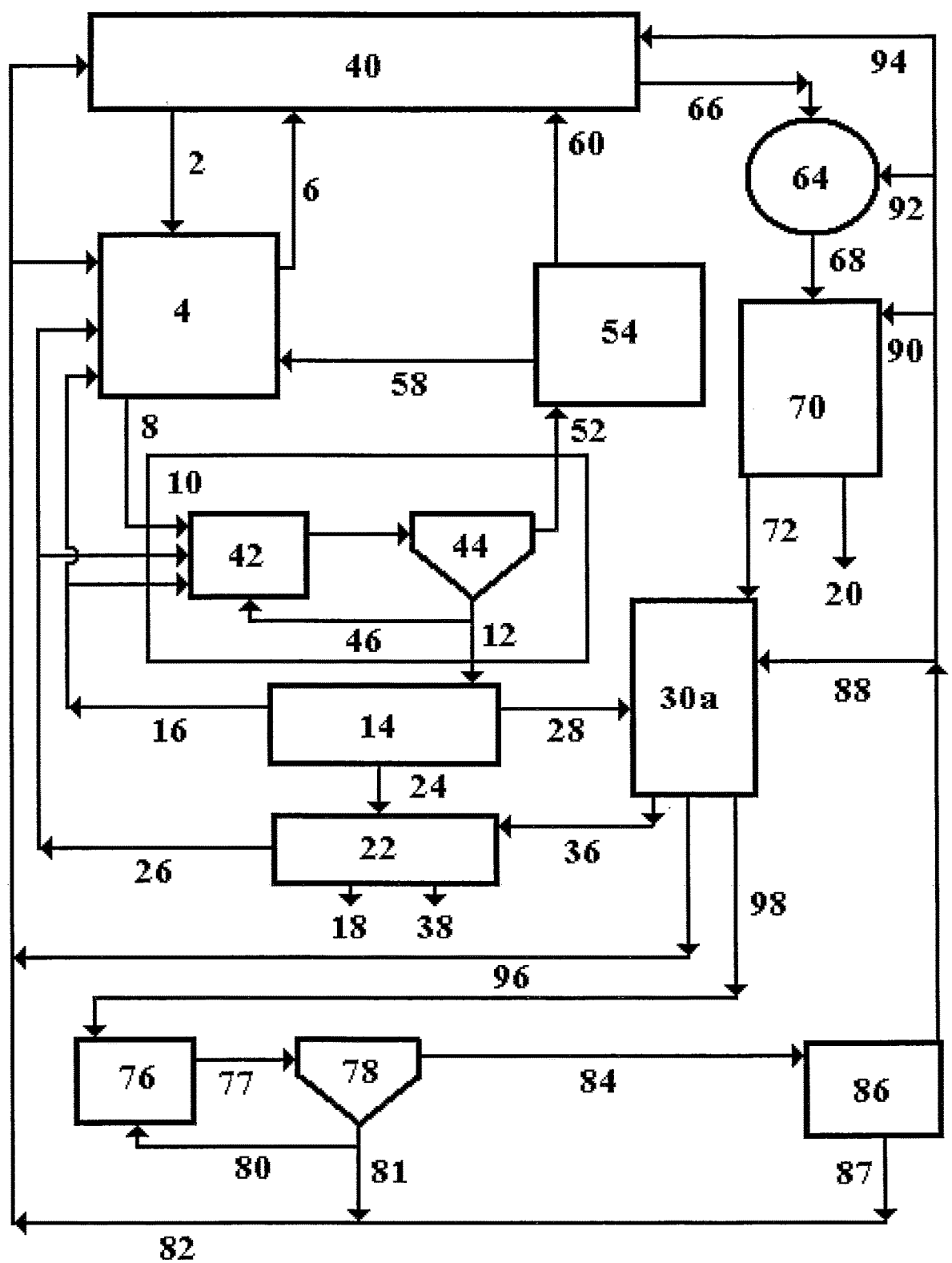
FIG. 8 is a schematic representation of a system including high nutrient concentrations in the harvested plant material degradation system and microbial growth system in accordance with an embodiment of the present invention.

In another embodiment shown in FIG. 8, the configuration allowing for high nutrient concentrations for the HPMD System 4 and Microbial Growth System 10, as shown in FIG. 7, is integrated with further wetland water polishing features for reuse in the Fish System 30a or Plant Production System 40, or for final discharge 20. In this embodiment the sand filter 86 effluent may be directed back to the Plant Production System 40 via 94 or may be directed to a collection pond 64 via 92, or a polishing wetland 70 via 90, or to the Fish System 30a via 88. The pond and polishing wetland can provide for additional water sequestering capability as well as for further improvement of water quality.

In another embodiment of the invention shown in FIGS. 9a and 9b, the HPMD System, Microbial Growth System, and the Intermediary Animal System described in earlier figures are each located in the same physical space to form a Combined System 123. In the Combined System, the HPMD System, the Microbial Growth System, the Intermediary Animal System, and the Product Animal System or Fish System are all combined in one contained volume such as a tank or pond with defined influent and effluent streams. In this embodiment the HPMD System may be confined to a part of the Fish Growing system, called the HPMD zone. The Microbial Growth System and the Intermediary Animal System may also be physically contained within, or will predominately reside within, the HPMD zone. The interface between the HPMD zone and the rest of the Product Animal System or Fish System will be such that water can freely flow between the two systems and that small fish can freely enter all or part of the HPMD zone to feed on microbes and intermediary animals which grow and reside within the HPMD zone. In one embodiment, larger product animals, such as fish, may be unable to enter the HPMD zone but will be able to feed on small fish and other intermediary animals which will grow within the HPMD and migrate out of this zone into the rest of the Product Animal System or Fish System.

Waste materials which collect at the bottom of the Fish System, particularly including fish excreta, can be collected and pumped as a recycle back to the HPMD zone where it can serve as a source of nutrients for the microbial degradation processes. In this embodiment the influent stream will enter the Fish System at some distance from the HPMD zone and the effluent stream will exit the total system through the HPMD zone.

As shown in FIGS. 9a and 9b, the Combined System 123 can be directly connected to a Fish System 130 in a manner so that fish can directly access and feed on the Intermediary Animals and microbial biomass produced in the Combined System 123.

Referring again to FIGS. 9a and 9b, the Fish System 130 may include a circular shallow fish tank or lined pond having a slightly sloped conical bottom. This may be directly connected to a tank or lined pond which would contain the Combined System 123. An influent water stream 100 may enter the fish tank at an angle inducing a slight circular movement of the water in the fish tank. An effluent stream 200 would leave the Combined System 123 area, preferably at a location furthest from the Fish System 130. Part of this effluent stream would be recycled via stream 150 back to the fish tank where it could be reintroduced at an angle so as to enhance the circular movement of the water in the fish tank.

In the Combined System 123, harvested plant material such as brush, branches, plant stalks, leaves, wood chips, and the like may be placed in an arrangement such that water and/or intermediary animals can penetrate the harvested plant material structures, i.e., to move in between branches. In one embodiment, aeration may be applied to the harvested plant material, such as at the bottom of the area where the harvested plant material is introduced such that the water surrounding the harvested plant material has a measurable dissolved oxygen level. Microbes may grow on the surfaces of the harvested plant material structures, thereby degrading the harvested plant material and creating new microbial biomass. Intermediary animals may then access and feed on this microbial biomass throughout the Combined System 123.

Generally, the harvested plant material in the Combined System 123 is submerged under water at all times. However, in some embodiments of the present invention, a portion, or even all, of the harvested plant material may be stacked above the water level. In these embodiments the harvested plant material may be periodically or continuously irrigated with water and/or nutrients to promote the growth of the microbial biomass.

Referring again to FIGS. 9a and 9b, the slight circular movement of the water in the fish tank of the Fish System 130 induced by the appropriate location and direction of the influent stream 100 and the system recycle flow 150 may allow fish excreta to be collected at the bottom or apex of the fish tank in the Fish System 130. From there it may be pumped via stream 160 back to the Combined System Area 123 where the fish excreta may be filtered out of the water by the harvested plant material. In the embodiments in which some or all of the harvested plant material is stacked above the water level, some or all of the recycled flow containing fish excreta and/or added nutrients are sprayed on to the top of the harvested plant material. This may be accomplished on a continuous or periodic basis such that the harvested plant material remains substantially wet to facilitate microbial growth. In these embodiments, blowers may be used instead of submerged aerators to supply adequate oxygen for the biological degradation of the harvested plant material.

The recycled wastes from the Fish System 130 may provide nutrients for the microbes degrading the harvested plant material. Additional nutrients could be added to this recycle stream to enhance the microbial degradation of the harvested plant material. In one embodiment, a fish access zone 135 can be provided to allow fish to enter the Combined System Area 123 to feed on the microbial biomass and the intermediary animals. Thus, the connection of the Fish System 130 to the Combined System Area 123 may be large enough to allow even large fish to easily pass between the two systems. By allowing this access, fish may feed on both the bacterial biomass and intermediary animals which live and grow in the Combined System Area 123.

In one embodiment, the system shown in FIGS. 9a and 9b can be constructed such that it is uncovered and open to the atmosphere, or covered with a greenhouse type structure or other material covering. Having this covering could retain heat within the system, which in cold climates could prevent freezing and could help maintain appropriate temperatures to promote the growth of microbes, intermediary animals, and product animals, such as fish. The covering could also prevent rainfall from entering the system or could reduce water loss from the system through evaporation.

In another embodiment of the present invention, the system shown in FIGS. 9a and 9b may be connected to a plant growing system or a water treatment system. This embodiment is shown in FIGS. 10a and 10b in which the effluent from the Combined System 123 is transferred via 140 to a Plant Growing System 145 including a shallow tank, lined pond, or natural pond where plants are grown in the water. These plants may include food plants such as watercress for cold climates or water chestnuts for warm climates, or they could comprise wetland plants adapted to the climate of the system. The plants could have a cleaning effect of the effluent stream, removing nutrients which the plants could use for growth, and filtering out particulate material. The Plant Growing System 145 could be uncovered or it could be part of a greenhouse structure which allows sunlight to enter for plant growth, or it could be covered by other structures which have artificial light to enable plant growth.

As shown in FIGS. 10a and 10b, structures may be placed in the Plant Growing System 145 to establish a long flow path which would produce a cleaner effluent, such as having a lower nutrient and/or particulate content, which could then be discharged 200 or recycled 150 back to the Fish System 130. The Plant Growing System 145 could contain several parallel but separate channels or flow paths such that one channel could be taken out of service for harvesting of plants, or cleaning and maintenance of the structure, without impairing the filtration and cleaning function from treating the effluent with alternative channels.

As shown in FIGS. 11a and 11b, the system shown in FIGS. 10a and 10b can be modified such that the effluent from the Fish System 130 passes through the Fish Access Zone 135 and is then directed through at least a part of the Combined System 123 before emerging as effluent for recycle 150 or discharge 200.

In another embodiment of the invention as shown in FIGS. 12a and 12b, the system shown in FIGS. 11a and 11b is connected via 140 to a further water treatment system 146 utilizing one or more of a variety of conventional wastewater treatment technologies. This may include, without limitation, activated sludge systems, trickling filter systems, rotating biological contactors, or other types of conventionally known treatment systems. It should be noted that the water treatment systems 145 and 146 may be interchangeably connected to the systems described in FIGS. 9a and 9b and 11a and 11b, and these systems could be covered or uncovered as a function of local conditions including climatic conditions.

Figure 13:
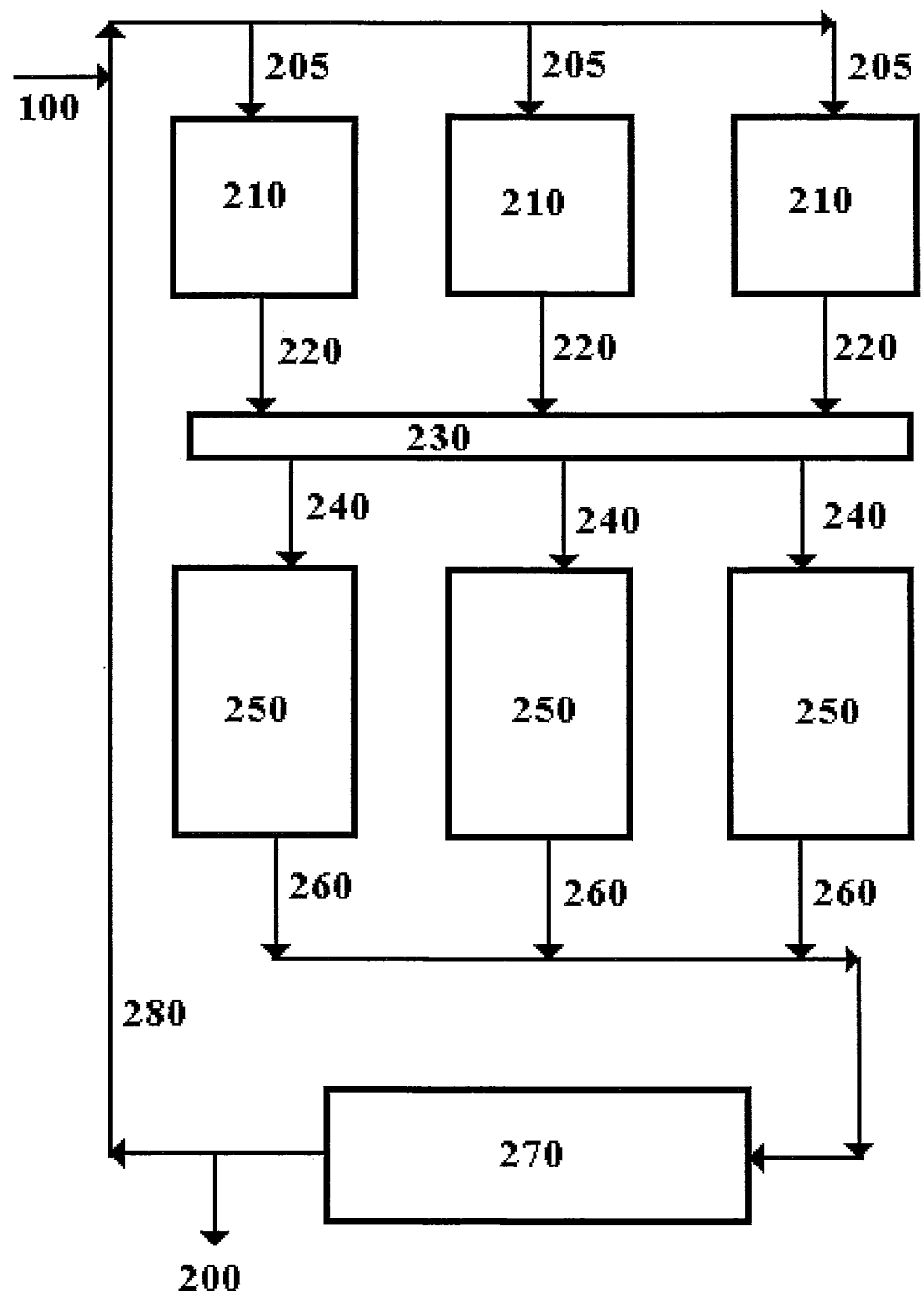
FIG. 13 is a schematic representation of a system including food production units in accordance with an embodiment of the present invention.

The systems of the present invention can also be utilized to create a fundamentally new method of producing food from natural environments. A preferred embodiment of this feature of the invention is shown in FIG. 13. Here a food, feed, or product animal, such as fish, is produced in one or more of a series of Food Production Units 210 which may include without limitation any of the systems previously described herein. These Food Production Units 210 can be located within a natural environment such as a forest, prairie, wetland, or the like and can use harvested plant material collected in an ecologically sustainable manner from these natural environments. This might include partial and periodic harvesting of plants and plant material at various times of year that would minimize or eliminate negative effects on wildlife inhabiting those environments.

The liquid effluents from the Food Production Units 210 may be transferred via 220 to a manifold, pipe, channel, canal or stream 230 and conveyed via 240 to a series of Plant Production Units 250 which could comprise flooded or irrigated fields, paddys, production wetlands or the like and which may be lined or unlined depending on soil conditions, water table elevation or other local conditions. These Plant Production Units 250 may be used for growing wild rice or watercress in cold climates or rice and water chestnuts in warm climates. Alternatively, any cultivated plant for which continuous or periodic flood irrigation is applicable could be used.

The effluents from the Plant Production Units 250 are collected via 260 in a final water polishing and distribution system 270. This unit may comprise a wetland, channel or canal that contains plants for filtration of particulate matter and removal of nutrients. The effluent from this final unit may be recycled via 280 and distributed via 205 to the Food Production Units 210, or may be discharged via 200 for use for irrigation in the containing natural environment or discharged to various bodies of water such as wetlands, ponds, streams, or the like within the containing natural environment.

All of the components of this system, except sometimes for the Plant Production Units 250, can be located within the natural environment that produces the harvested plant material used by the system. Thus the Food Production Units 210 and the various wetlands, channels, canals and the like represented by 230 and 270 could reside underneath a forest or savannah canopy or the weeds, grasses, bushes and shrubs of various wetland or grassland environments. This would allow significant food and feed production from land currently not used for agricultural production of food and feed and could do so in a manner that would sequester much greater amounts of carbon and water than is possible with conventional agricultural land which is used for the cultivation of grain and vegetable crops.

The above mentioned component systems can be connected via a variety of forward flows whereby the products of the component are transferred to the next system component, and by a series of recycle flows whereby the component byproducts and animal excreta are recycled back to prior components for reutilization within the production process.

In one embodiment the recycle flows originates with the Intermediary Animal System, the Processing System, the Fish System, or the Aeration Wetland, and is directed to the Microbial Growth System, the Harvested Plant Material Degradation System, or the Photosynthetic Production System. The selection of destinations and the partitioning of flows if more than one destination is chosen can be a major part of the management and control system for the total process.

A system of mass balance accounting is also used to control and manage the production process. This mass balance approach will track some or all of the following chemical elements; carbon, hydrogen, oxygen, nitrogen, phosphorus, sulfur, sodium, potassium chloride, calcium, magnesium, iron, manganese, copper, zinc, and nickel. In general carbon dioxide and water will be fixed into plant material (carbohydrate, cellulose, etc.) in the Photosynthetic Production System. Minerals, salts, and nutrients will be extracted from the earth in the fields and wetlands, and a series of products including fish, feeds, and processed foods will be removed from the system. To balance the elements removed in the products nutrients and minerals will need to be added to maintain the chemical balance in the production lands and in the system itself.

Because parts of the system are open to the surrounding environment it is necessary to maintain a water balance throughout the system. Rain, snow and other forms of precipitation will enter the system and evaporation and evapotranspiration will remove water from the system. Any imbalance in the water inventory will be compensated for by either adding water from an external source or discharging excess water to the environment. If excess water must be discharged it usually will come from the effluent flow from the Microbial Growth System which will pass through an aeration wetland or a filter (such as a sand filter). The excess water will then be further treated by land applying it to the Production Fields where it may overflow into a Collection Pond or by discharging it directly to a Collection Pond or a treatment wetland. Once there it will normally flow through a final polishing wetland and then be discharged to the environment. Other forms of water treatment technology may be applied to meet mandated discharge water quality criteria.

In a further embodiment of the invention, a structure for the production of aquatic organisms that controls water quality and manages the uneaten food and wastes produced by the aquatic organisms. The structure may comprise a tank, pond, or some bounded region of a lake, stream, ocean, or other body of water. The invention also comprises components which may be introduced into a tank or pond, or some bounded region of a lake, stream, ocean, or other body of water. These components can facilitate the production of aquatic organisms without causing the pollution of the bounded body of water, or of a larger aquatic environment within which such body of water is contained, from the wastes produced by the aquatic organisms or by uneaten food fed to the aquatic organisms.

The system of the present invention may use plant material (Plant Material) produced by a photosynthetic reaction in plants, as described previously. Generally the material will comprise Plant Material grown in forests or woodlots and will include whole trees and bushes, logs, branches, leaves, and roots. Plant Material may also be produced within a given aquatic environment and could include algae, phytoplankton, seaweeds, and a variety of other higher plants which are either rooted in submerged soil, mud, or muck; floating with parts of the plant at or near the surface; or submerged but not rooted in soil. Plant Material may also include grasses, reeds, shrubs, bushes, yard wastes, and a variety of agricultural products and byproducts such as corn stover, straw, hay, vegetable and fruit processing waste, etc. Plant Material may also include various produced or manufactured materials and products such as lumber, paper, cardboard, fabric, and the like.

In this embodiment of the invention the Plant Material is placed into the tank, pond, or other constrained body of water. Usually the Plant Material is introduced in small particles which may be produced by a mechanical process such as grinding, shredding, chipping, chopping or other similar processes. The Plant Material may be further constrained by being placed into a net, screened bat, or other confined area which is constructed in such a way that water from outside of the constrained area may move through the constrained area thereby coming in contact with the Plant Material. This process may be facilitated by pumps, mixers, aeration devices, or other similar means.

The Plant Material is then subjected to a microbial treatment process in which various constituents of the Plant Material are converted into a microbial cell mass or oxidized. The constituents most generally converted in this manner usually include cytoplasmic sap comprising proteins, nucleic acids, fats, oils, sugars and other molecular components of the plant cells, and the more easily digested fraction of the structural components of the Plant Material such as cellulose or parts of the hemicellulose fraction of the plant material. This microbial process will consume nutrients such as nitrogen, phosphorus, and sulfur that will be contained within the water both in soluble and particulate form as a result of the excretion of wastes by the aquatic organisms and as a result of non eaten food fed to the aquatic organisms. The result is that the constrained Plant Material and its resident microbial biomass act as a water filter and purification system.

As part of the bioconversion process microbes and part of the microbial biomass may be continually or intermittently removed from the Plant Material. This may occur through the use of other biological organisms such as small fish, insects, snails, worms, or other macroinvertebrates. These organisms may have continuous or intermittent access to the constrained Plant Material during which time they may collect or consume the microbes. The organisms may leave the constrained Plant Material in which case they may serve as food for the produced aquatic organisms. If they do not serve as food for the produced aquatic organisms they may be removed from the system by various mechanical or other means.

Figure 14:
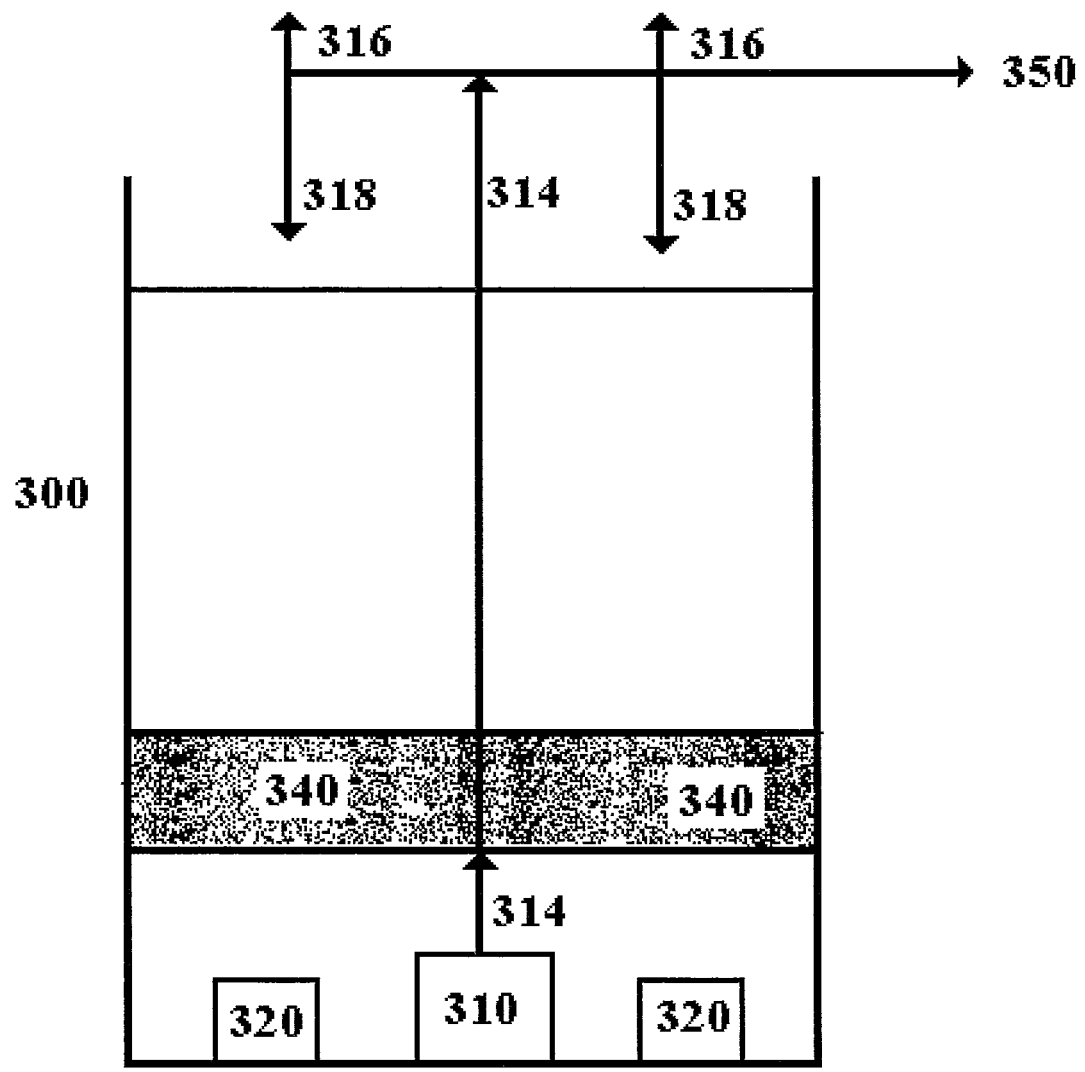
FIG. 14 is a schematic representation of a cross-sectional front view of a tank having a plant material bat separating liquid regions within the tank into a first and a second zone in accordance with an embodiment of the present invention.

In one embodiment of the invention as shown in FIG. 14 a tank 300 contains water and one or more production aquatic organisms. The tank contains one or more water pumps 310, usually located on the bottom of the tank, that pump water from the bottom to the top of the tank via line 314. The pumped water may be sprayed into the air via lines 316, thereby providing for aeration, or it may be discharged at or near the surface of the water via lines 318, or it may be discharged via line 350. One or more aerators 320 may also be located in the tank, and again these are usually placed on the bottom of the tank. Small particulate plant material is placed within a bat 340 which is comprised of structural material such as wood and some form of netting or screening which is able to contain the plant material within the dimensions of the bat.

In this embodiment of the invention, the bat 340 comprises an elevated floor near to the tank bottom. This floor is such that it separates the water in the tank into two zones. One zone is relatively small and located near the tank bottom. The pumps and aerators are located in this zone. The other upper zone is relatively large, comprising all of the rest of the tank except for the lower zone and the bat, and contains the production aquatic organisms. The water pump(s) pump water from the lower zone to the top of the upper zone. This action causes water to flow from the upper zone, through the bat, and into the lower zone. The aerators which are located in the lower zone emit air which then bubbles through the bat and the upper zone until it reaches the water surface. This activity maintains an adequate dissolved oxygen level to support the growth of the production aquatic animal(s) in the upper zone and also to support the aerobic microbial growth which takes place within the plant material contained within the bat.

Uneaten feed and excreted solid wastes from the production aquatic animals falls through the upper zone and is deposited on the upper surface of the bat. These uneaten feeds and wastes are then acted on by the microbial biomass within the bat and the nutrients contained in the uneaten feeds and wastes are utilized by the bat's microbial biomass to grow new microbes and degrade the plant material. Dissolved wastes, and in particular the nutrients such as nitrogen (usually as ammonia) and phosphorus (usually as ortho phosphate) excreted by the production aquatic animals are filtered out of the water as it passes through the bat. These soluble nutrients are removed by and incorporated into the growing microbial biomass living within the bat.

Small Intermediary Animals such as worms, snails, insects, mollusks, and the like may be introduced into the bat to eat some of the microbial biomass produced therein. These small intermediary animals may expose themselves on the upper surface of the bat to the production aquatic animals which may eat them. This can represent an additional food source for the production aquatic animals and serve to reduce feed costs associated with their production.

Once the microbial conversion of the Plant Material within the bat has progressed to a certain level, the bat is removed and replaced with a new bat containing fresh Plant Material. The material remaining in the removed bat is then prepared for other uses such as energy production.

Figure 15:
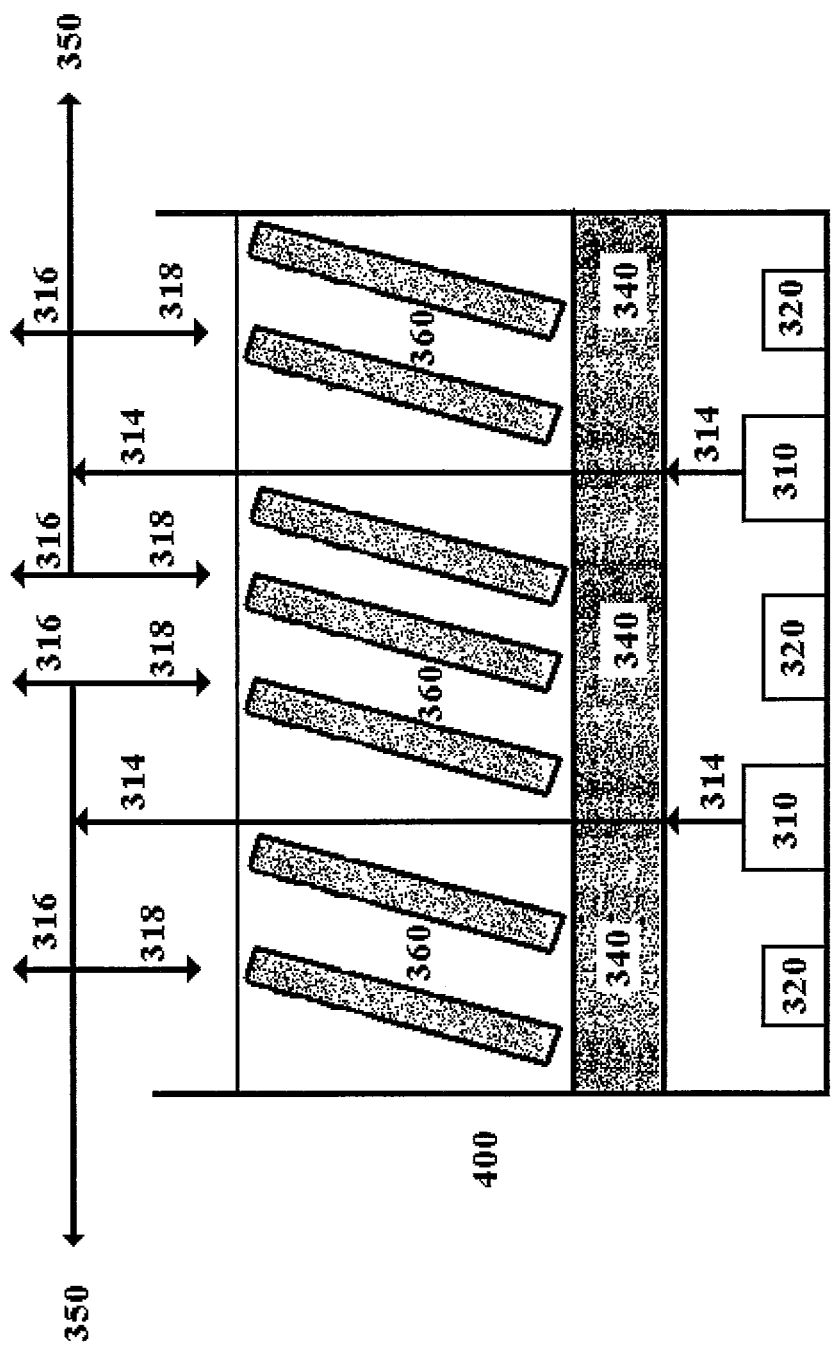
FIG. 15 is a schematic representation of a cross-sectional front view of a tank having a plurality of plant material bats separating liquid regions within the tank in accordance with an embodiment of the present invention.

In another embodiment of the invention the tank shown in FIG. 14 may be expanded by the addition of additional aerators, pumps and spray piping and may be further enhanced by the addition of other more bats containing Plant Material. This configuration is shown in FIG. 15 as tank 400. The additional bats 360 may be placed at various locations within the upper zone and may be angled, shaped, and configured so as to provide additional water treatment and food for the production aquatic animals.

Figure 16:
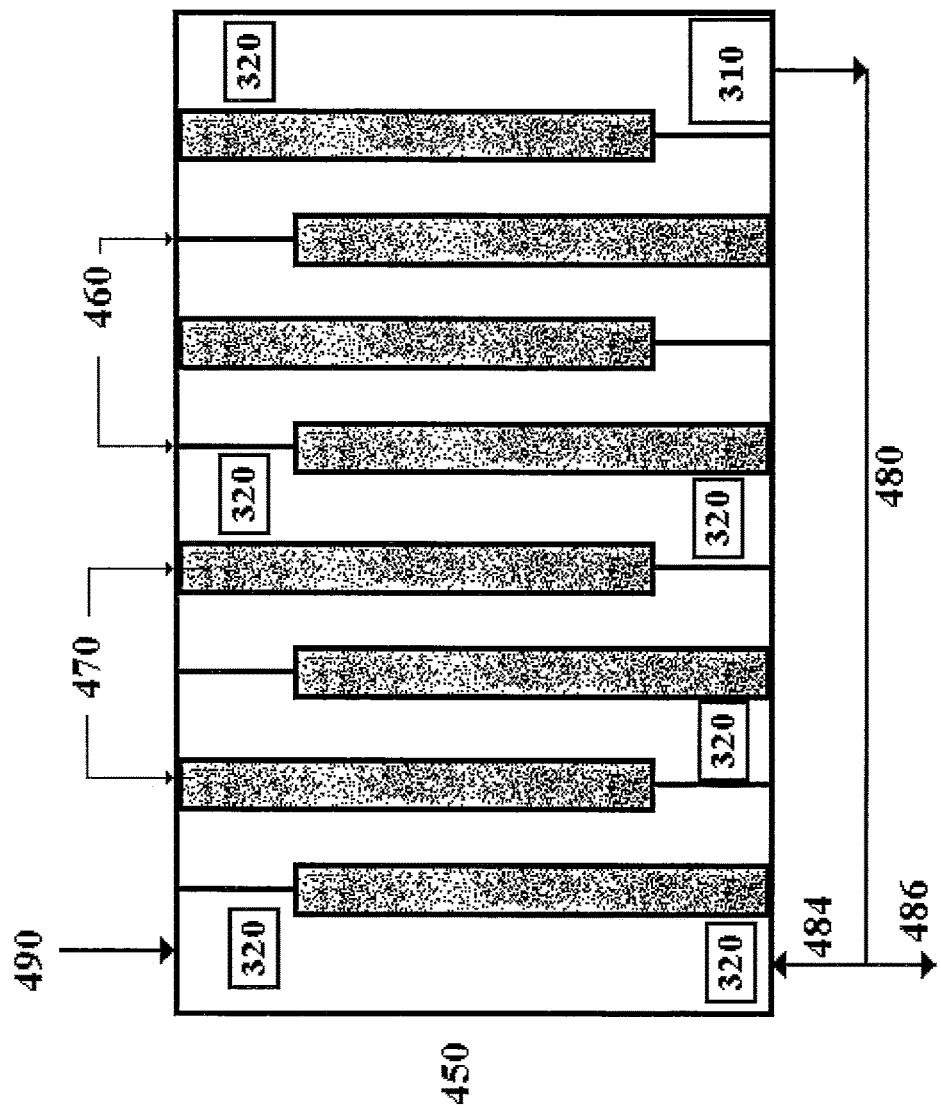
FIG. 16 is a schematic representation of a cross-sectional front view of a tank having a plurality of plant material bats and a plurality of slide gates in accordance with an embodiment of the present invention.

In yet another embodiment of the invention as shown in FIG. 16, the bats 470 may be placed in a horizontal manner in a rectangular tank 450. By adding a pump 310 at one end which recycles water via lines 480 and 484 from that end back to an opposite end, water will flow through or along side of the bats thereby allowing for nutrient and waste removal from the water. By placing slide gates 460 at alternating ends of the bats 470 a serpentine flow pattern can be established and this can be alternated with a flow passing through the bats by appropriate manipulation of the slide gates. Aeration may be introduced at various locations within the tank to facilitate growth of the production aquatic animals and microbial biomass. Alternatively, the slide gates may be omitted so that flow must go through each of the bats 470. Aeration may be supplied by aerators 320 located throughout the tank and these aerators may be underneath some of the bats 470.

Figure 17:
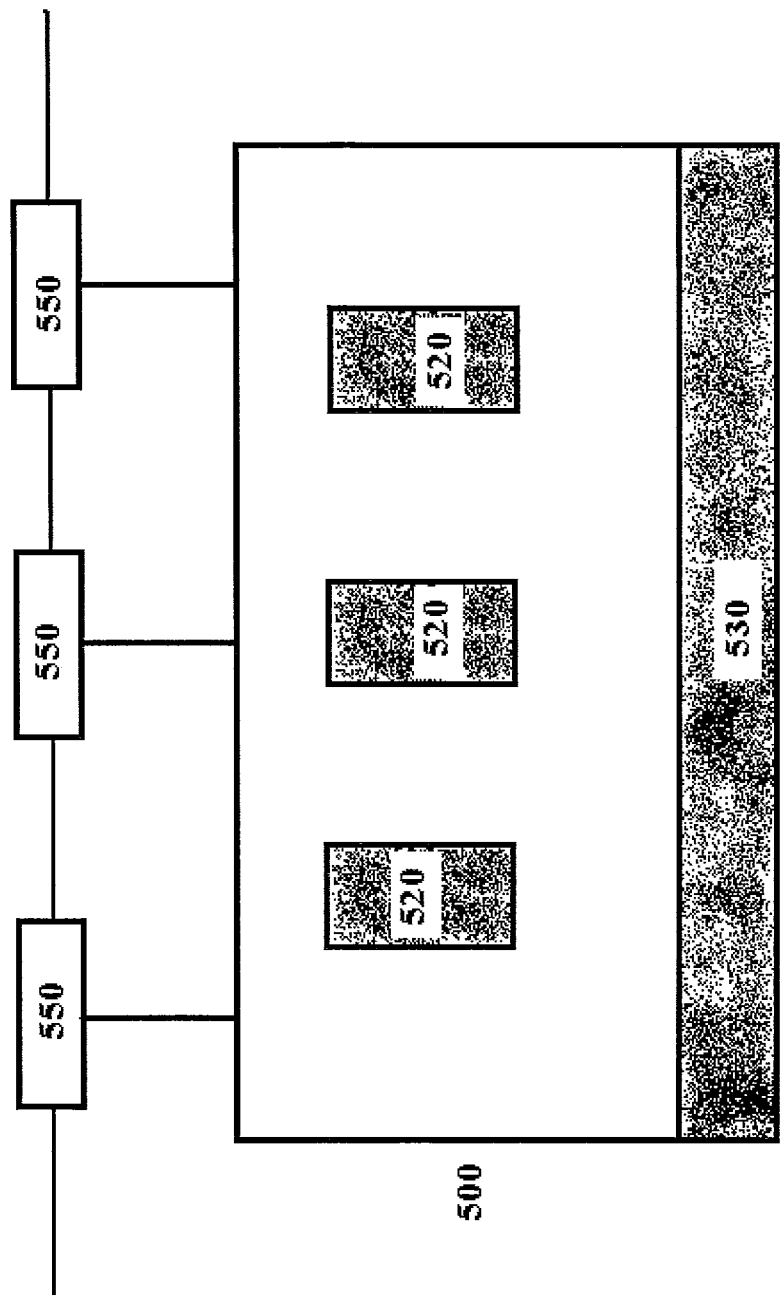
FIG. 17 is a schematic representation of a front view of a system contained within a free-form body of liquid including a plurality of floats, submerged pens, and plant material bats in accordance with an embodiment of the present invention.

In yet another embodiment of the invention as shown in FIG. 17 a containment structure 500 such as a cage, pen, net or the like may be introduced into a larger body of water such as a lake, stream, pond, or ocean. The containment structure may be supported from floats 550, as shown, or may be anchored to the shore or bottom of the larger body of water in some appropriate manner. If this containment structure is used for the production of aquatic animals the wastes from such animals, and any uneaten food fed to these animals will normally be allowed to escape the containment structure thereby polluting the surrounding larger body of water.

By introducing Plant Material Bats, as described above as 530 on the floor of the containment structure, or as described above as suspended within or near to the containment structure, the wastes and uneaten food may be absorbed by the microbial biomass contained within the bats. This can reduced water pollution associated with the aquatic animal production. If the bats are located within the containment structure, and if appropriate small intermediary animals are introduced into the bats, or if small intermediary animals indigenous to the larger body of water are allowed to colonize the bats, a supplemental feed may be provided for the production aquatic animals. If the bats were extensive enough, and if additional nutrients were supplied, all of the feed required for the production aquatic animals could be supplied.

Another embodiment of the present invention will consist of the implementation of a system for the production of aquatic organisms that controls temperature, photoperiod, and water quality and manages the uneaten food and wastes produced by the aquatic organisms. In general the system will consist of three tanks cyclically connected in a variety of ways or multiples thereof. These components can facilitate the production of aquatic organisms without causing the pollution of water from the wastes produced by the aquatic organisms or by uneaten food fed to the aquatic organisms.

The system uses plant material (Plant Material) produced by a photosynthetic reaction in plants. Generally the material will comprise Plant Material grown in forests or woodlots and will include whole trees and bushes, logs, branches, leaves, and roots. Plant Material may also be produced within a given aquatic environment and could include algae, phytoplankton, or seaweeds. Other forms of Plant Material may also include grasses, reeds, shrubs, bushes, yard wastes, and a variety of agricultural products and byproducts such as corn stover, straw, hay, vegetable and fruit processing waste, etc.

In general the Plant Material is placed into two of the three tanks. Usually the Plant Material is introduced in small particles which may be produced by a mechanical process such as grinding, shredding, chipping, chopping or other similar processes. The Plant Material may be further constrained by being placed into a net, screened bat, or other confined area which is configured in such a way that water may move through the constrained area thereby coming in contact with the Plant Material. This process may be facilitated by pumps, mixers, aeration devices, or other similar means.

The Plant Material is then subjected to a microbial treatment process in which various constituents of the Plant Material are converted into a microbial cell mass or oxidized. The constituents most generally converted in this manner usually include cytoplasmic sap comprising proteins, nucleic acids, fats, oils, sugars and other molecular components of the plant cells, and the more easily digested fraction of the structural components of the Plant Material such as cellulose or parts of the hemicellulose fraction of the plant material. This microbial process will consume nutrients such as nitrogen, phosphorus, and sulfur that will be contained within the water both in soluble and particulate form as a result of the excretion of wastes by the aquatic organisms and as a result of non eaten food fed to the aquatic organisms. The result is that the constrained Plant Material and its resident microbial biomass act as a water filter and purification system.

Figure 18:
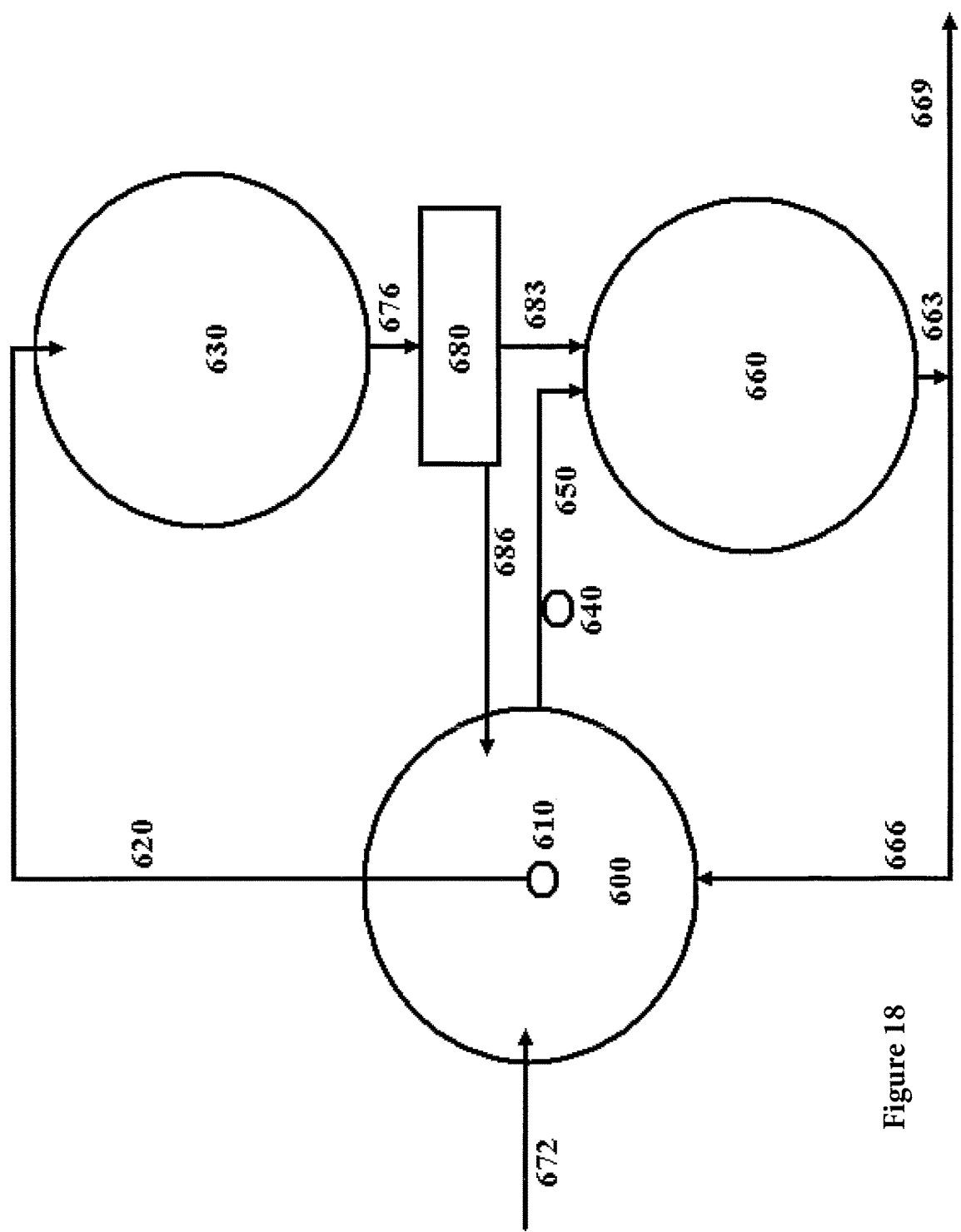
FIG. 18 is a schematic representation of a top view of a three tank system for raising fish in accordance with an embodiment of the present invention.

As part of the bioconversion process microbes and part of the microbial biomass may be continually or intermittently removed from the Plant Material. This may occur through the use of other biological organisms such as small fish, insects, snails, worms, or other macroinvertebrates. These organisms may have continuous or intermittent access to the constrained Plant Material during which time they may collect or consume the microbes. The organisms may leave the constrained Plant Material in which case they may serve as food for the produced aquatic organisms. If they do not serve as food for the produced aquatic organisms they may be removed from the system by various mechanical or other means. The basic system configuration is shown in FIG. 18.

The system comprises three main process units each contained within its own tank or vessel as follows: Tank 600 is a fish raising tank which will contain the product fish produced by the system. It will have an adequate source of aeration provided by several fine bubble diffusers located throughout the tank or some other equivalent aeration system. A pumping system, shown as Pump 610, capable of intermittent operation will be located at the center bottom of the tank. This pump will operate on a timed basis and will be a positive displacement pump capable of removing the fish solid wastes from the tank. The discharge from 610 will go via line 620 into a second tank, bin, or trickling filter 630.

There will be a second pump, 640, associated with Tank 600 and this pump or its suction line will be located close to the water surface near the tank wall. This pump will run continuously and will be capable of maintaining a hydraulic detention time (HRT) within Tank 600 of two to three hours, or longer, by pumping water from Tank 600 through line 650 into a third tank or submerged filter 660. Part of the pumped water may be sprayed into the air thereby providing for aeration. After passing through Tank 660 the water will flow by gravity via lines 663 and 666 back into Tank 600.

A small fraction of the effluent from Tank 660 may be discharged from the system as a final system effluent via line 669. Tank 660 will also receive a relatively small flow 672 of clean fresh water which will serve as a system influent flow. The system effluent fraction 669 from the Tank 660 discharge will be approximately equal to the influent flow 672 into Tank 600.

The water and wastes collected by Pump 610 are pumped to Tank 630 which contains harvested plant material as previously described, usually in the form of chips or other forms of small pieces such as sticks or twigs. Tank 630 normally will contain the plant material in a pile or pack which is continually or intermittently sprayed or irrigated with water and wastes from Tank 600. The water will trickle down through the pile or pack of plant material and will then be directed to Tank 600 or Tank 660. Usually the solid wastes which are pumped by Pump 610 will be captured by the plant material in Tank 630 so that Tank 630 will act as a filter to remove these wastes from the water stream.

Microbes will live on the surfaces of the plant material in Tank 630 and these will capture dissolved nutrients in the influent stream 620 from Pump 610. Various invertebrates will also live within Tank 630 and these will eat the microbes on the surfaces of the plant material. Excess invertebrates will often be washed out of Tank 630 by the irrigation stream from Pump 610.

The effluent stream from Tank 630 will flow via line 676 into a solids and organism selector 680 and from there it will usually flow via line 683 into Tank 660. The selector will be a screen or similar device so that most of the water in the effluent stream from Tank 630 will pass through the screen into Tank 660. The remaining water, and any solids or organisms larger than microbes that are retained by the screen, will normally be directed back into Tank 600 via line 686. In general the screen will be configured so that organisms leaving Tank 630 can migrate on their own into Tank 600. Other configurations can be elected so that the solids and organisms from Tank 630 can be collected for other use or mechanical delivery to Tank 600. Any solids that are passed into Tank 600, and that are not eaten by the organisms in Tank 600, will be subsequently collected by Pump 610 and returned to Tank 630.

Figure 19:
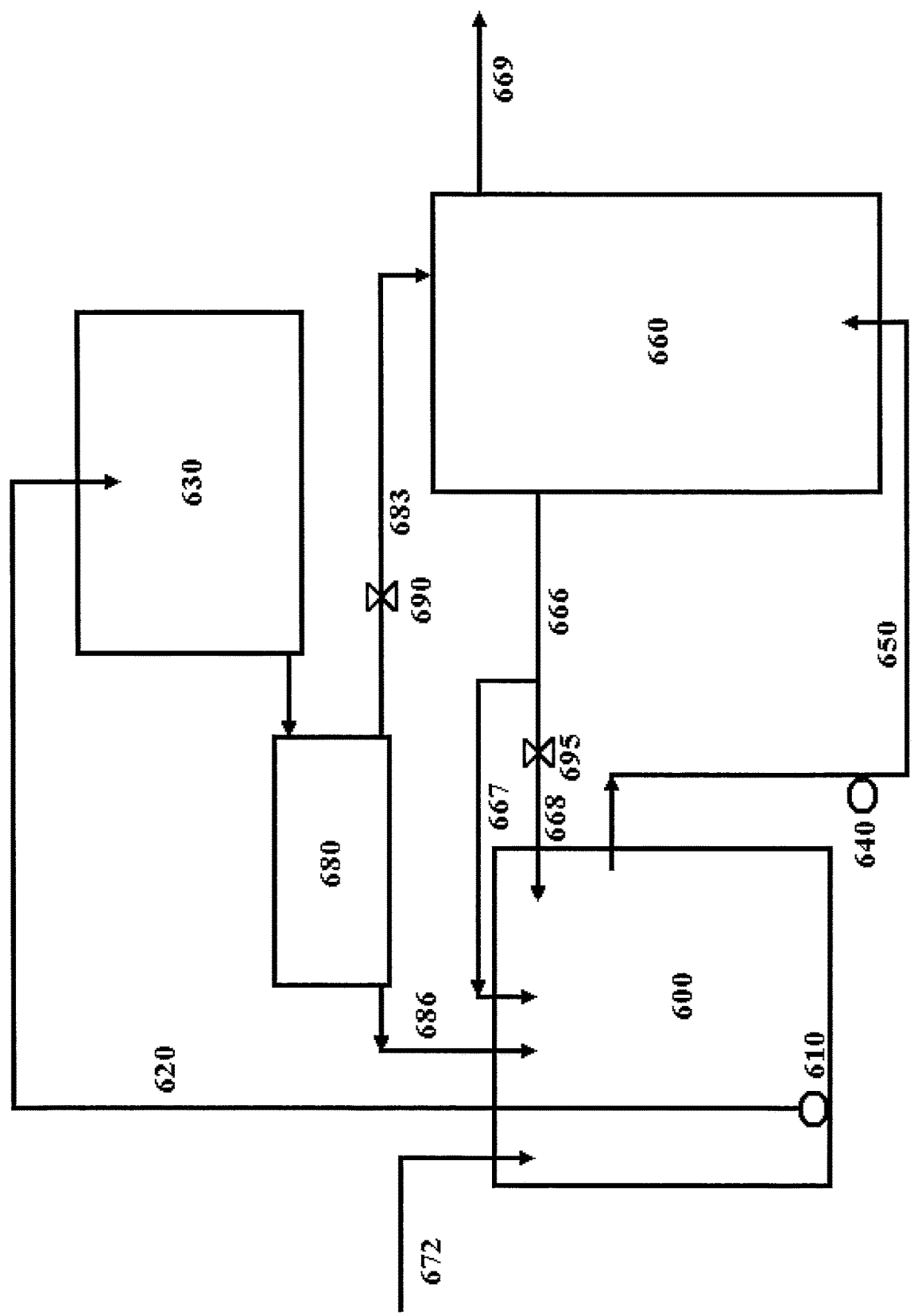
FIG. 19 is a schematic representation of a cross-sectional side view of a three tank system for raising fish in accordance with an embodiment of the present invention.

It is often desirable to have Tank 630 elevated relative to the water surface of Tank 600, so that the invertebrate containing effluent stream from Tank 630 may flow by gravity into Tank 600 or Tank 660. This is shown in FIG. 19 which is a side view of the configuration shown in FIG. 18. In some configurations Tank 630 may be located partially or completely above Tank 600 or Tank 660, or both.

In other configurations where Tank 630 is not elevated relative to Tanks 600 and 660, a pump may be used to return the effluent from Tank 630 back to Tank 600 or Tank 660. Air may be passed around and through the plant material in Tank 630 and this may be assisted through the use of a mechanical blower or the like. Air may also be injected into the stream pumped by Pump 610 so that it contains a relatively high dissolved oxygen content. These various configurations will insure that the organism environment in Tank 630 is normally aerobic.

In some configurations of the system the pile or pack of plant material in Tank 630 may be continually or periodically submerged. In these configurations the aqueous stream from Pump 610 may enter the bottom of Tank 630 and overflow the top and then be returned to Tank 600, or the aqueous stream from Pump 610 may enter at the top of Tank 630. In this latter case the effluent from Tank 630 will exit from the bottom of the tank and will usually be pumped back into Tank 600. Usually the effluent will exit Tank 630 from an opposite side from that receiving the influent stream.

If the environment in Tank 630 is submerged then aeration will usually be supplied through the use of blowers or aerators which inject air into the bottom of Tank 630. The environment water for the production of the product aquatic organisms that is removed from Tank 600 by Pump 640 is recycled through Tank 660 and then returned to Tank 600.via line 666. Tank 660 will normally be filled with water and will contain plant material in various configurations as was described for Tank 630. Tank 660 will also be aerated so that oxygen is available for the organisms in the tank. The growth of the microbes and invertebrates in Tank 660 will remove dissolved nutrients from the aqueous stream pumped into Tank 660 by Pump 640. Thus Tank 660 will act as a biofilter for such dissolved nutrients. Any suspended solids in the aqueous stream will also be removed in Tank 660.

Normally the water will enter Tank 660 in a location which is opposite to or at some significant distance from the outlet of the tank. Usually this effluent stream will exit the tank at a location which is maximally distant from the influent location to the tank. The effluent from Tank 660 will usually flow by gravity back into Tank 600. Excess water in the total system will exit the system as a fraction of the effluent flow from Tank 660. In this way the system effluent will balance the system influent minus any evaporative losses. In all of these configurations the flow 620 from Tank 600 to Tank 630 will be significantly less than the flow 650 from Tank 600 to Tank 660. This differential can be as much as one to two orders of magnitude.

In the configuration shown in FIG. 19 two valves have been added to allow for flow control and direction options. Valve 690 can be used to divert all of the effluent from Tank 630 back into Tank 600, or allow some or all of the screened effluent from Tank 630 to flow by gravity into Tank 660. Valve 695 can regulate how the flow from Tank 660 enters Tank 600. When Valve 695 is closed the effluent from Tank 660 enters Tank 600 via line 667 above the surface level in Tank 600 and this will generate additional aeration. When Valve 695 is open the flow from Tank 660 enters Tank 600 via line 668 at or just below the surface of Tank 600. This will provide minimal to no aeration but will allow invertebrate organisms or small fish such as minnows to migrate from Tank 660 into Tank 600.

One of more species of fish will be introduced into Tank 600. A highly diversified microbial population will be introduced into Tanks 630 and 660. The microorganisms comprising this innoculum will normally be derived from local populations occurring in the environment close to a system location. Sources for these microbes will be local streams, ponds, wetlands, grasslands, forests, and the like.

A number of small intermediary animals will also be introduced into Tanks 630 and 660. These will include a variety of invertebrates obtained from the local environment in much the same manner and from the same general sources as was used in the case of the microbial innoculum. These organisms could include local pond snails, a number of aquatic worms including oligochates, a variety of insect larvae, and possibly crayfish. Small fish such as minnows may also be included.

The operational protocol comprises feeding the fish in Tank 600 a commercial feed. Feeding will be done once a day and the fish will be fed to satiation. Excess Small Intermediary Animals raised in Tanks 630 and 660 will be allowed to migrate into Tank 600 where they may serve as food or a feed supplement for the trout. A supplemental nutrient source may be introduced into the influent side of Tanks 630 and 660. As the minnow and invertebrate populations grow and migrate into Tank 600 the commercial feed will be reduced and in the preferred embodiment of the invention eventually totally eliminated.

Figure 20:
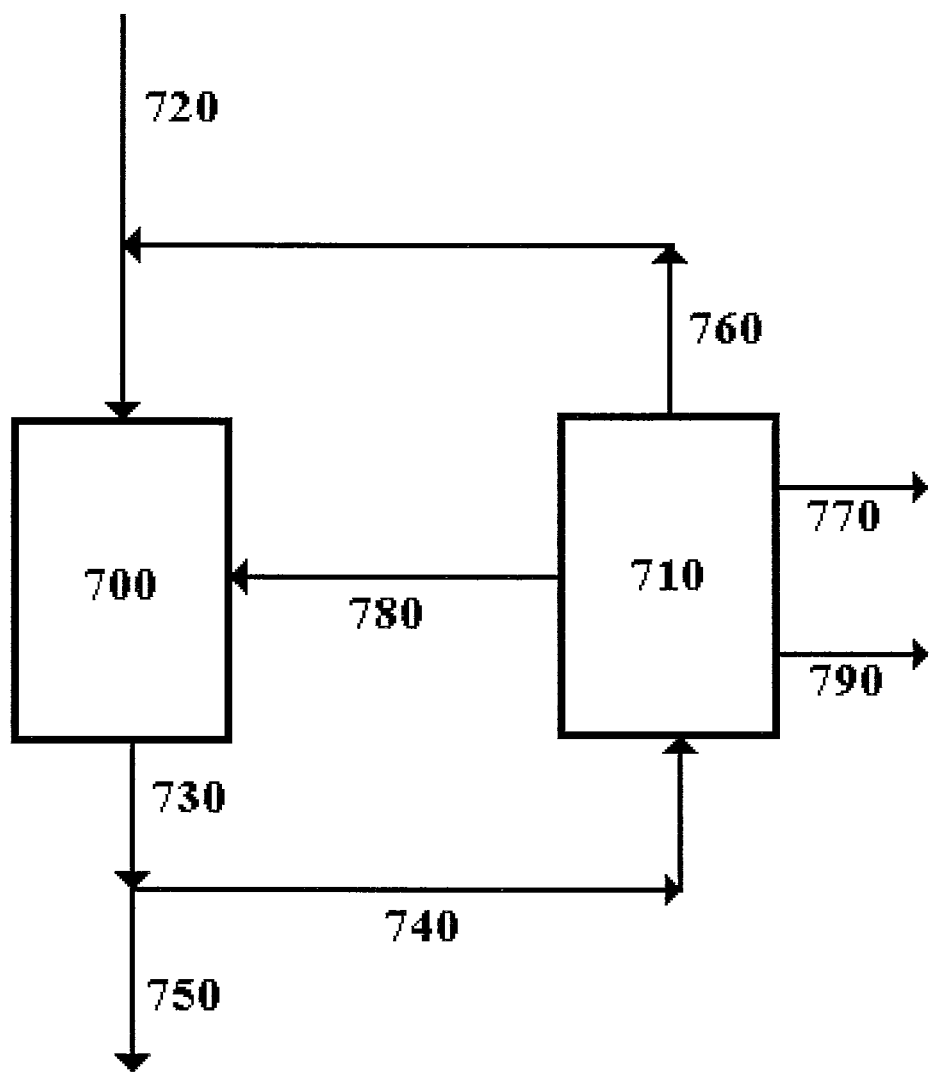
FIG. 20 is a schematic representation of a system in which an animal raising system is coupled with an embodiment of the invention which performs water treatment, wastewater treatment, waste treatment, and/or feed generation for the animal raising system.

In a further embodiment of the invention, as shown in FIG. 20, an animal raising facility 700 may be provided as a source of inputs to various other embodiments of the system 710, such as those including one or more of the system elements shown and described with reference to FIGS. 1-19. As shown in FIG. 20, the invention as described relative to 710, with reference to FIGS. 1-19, may be used as a water, wastewater, or waste treatment process for wastes or other materials produced in the animal raising facility 700. The animal raising facility 700 includes at least one species of animal. In one embodiment, the animal raising facility 700 may be any conventional aquaculture production facility such as, for example, a flow through fish raising facility and/or a recirculating aquaculture system. In another embodiment, the animal raising facility 700 may be a conventional terrestrial animal production facility, such as a dairy, beef, pork, poultry, veal, and/or lamb production facility.

As shown in FIG. 20 the animal raising facility 700 receives inputs of water and feed 720. The animal raising facility 700 produces an effluent stream 730 which contains wastes produced by the animals contained within the animal raising facility 700. Usually these wastes are suspended in a substantially aqueous fluid. In most modern agricultural production practices most or all of the wastes and effluent water and wastewater are discharged to the environment or used for crop irrigation 750. In some cases, such as recirculating aquaculture systems or flush confined animal feeding operations (CAFOs), as are conventionally known, a portion of the waste and effluent stream is recycled via effluent 740 and intake 760 back to the beginning of the animal raising system 700. In this embodiment, the effluent 740 of the animal raising facility 700 is directed to the system 710, for subsequent treatment by the system 710. In one form of this embodiment, the effluent 740 of the animal raising system 700 may be incorporated as part of the feed stock for the Harvested Plant Material Degradation (HPMD) System 4, or as a feed stock for the microbial biomass within the Microbial Growth System 10, as described above in detail with reference to FIG. 1.

In another embodiment, the wastes suspended or dissolved within the effluent 740 of the animal raising system 700 may be used as a nutrient source, particularly as a source of nitrogen and phosphorus, for the microbial processes that at least partially degrade the harvested plant material within the Harvested Plant Material Degradation (HPMD) System 4, as described in detail with reference to FIG. 1. In another embodiment, the wastes suspended or dissolved within the effluent 740 of the animal raising system 700 may be used as a nutrient source, particularly as a source of nitrogen and phosphorus, for the microbial processes that comprise the Microbial Growth System 10, as described in detail with reference to FIG. 1.

In another embodiment of the present invention the wastes suspended within the effluent 740 of the animal raising system 700 and/or the substantially aqueous portion of the effluent 740 may be treated within the system 710, as described herein. The treated effluent of the system 710 may be directed to the intake 760 of the animal raising system 700 as clean water for reuse within the animal raising facility 700. Alternatively, the effluent of the system 710 may be directed to the environment or for irrigation 770 on land as clean water. As used herein, the term "clean water" means a substantially aqueous fluid having at least a portion of the solid and nutrient waste removed therefrom by treatment by the system 710 described herein.

In yet another embodiment, intermediary animals and/or product animals, as previously described herein, produced within the system 710 may be returned to the animal raising facility 700 as feed 780. In another embodiment, intermediary animals and/or product animals, as previously described herein, may be exported as animals or feed 790 for sale or use outside of the connected animal raising facility 700.

Figure 21:
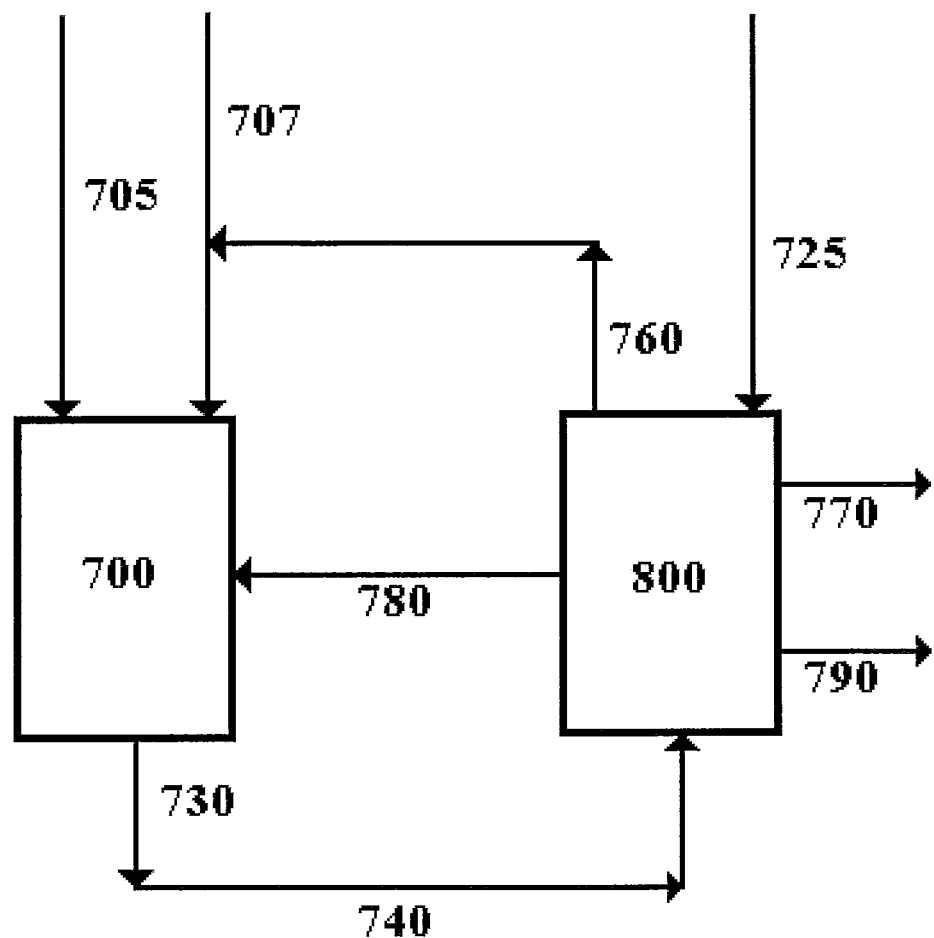
FIG. 21 is a schematic representation of a system in which a recirculating aquaculture system is coupled with an embodiment of the invention which performs water treatment, wastewater treatment, waste treatment, feed generation, or some combination of these functions, for the recirculating aquaculture system.

In yet another embodiment, as shown in FIG. 21, a recirculating aquaculture system is coupled to one or more previously described embodiments of the invention 800 such as those shown in FIG. 3, 9, 10, 11, or 12. As shown in FIG. 21 the recirculating aquaculture system 700 receives inputs of feed 705, and water 707. Water and wastewater containing solid and dissolved wastes are recycled from the recirculating aquaculture system 700 via stream 730 to the system 800. By passing through the Harvested Plant Material Degradation (HPMD) System 4, and the Microbial Growth System 10, as described relative to FIG. 3, the solid and dissolved wastes, particularly including the nutrient fraction of those wastes, will be at least partially removed from the liquid fraction of the recycled stream and will be incorporated within a microbial biomass. Alternatively, by passing through the Combined System 123 or the HPMD zone of the process of the invention, as shown in and described in detail relative to, FIGS. 9*a* & 9*b*, FIGS. 10*a* & 10*b*, FIGS. 11*a* & 11*b*, and FIGS. 12*a* & 12*b*, the solid and dissolved wastes, particularly including the nutrient fraction of those wastes, will be at least partially removed from the liquid fraction of the recycled stream and will be incorporated within a microbial biomass.

Referring again to FIG. 21, the various embodiments of the invention as shown in 800 will receive, as inputs, Harvested Plant Material as previously described and delivered via 725. Clean water as produced from 800 will be recycled to the animal raising system 700 via the stream 760, or, in the event of excess water within the system, discharged to the environment or irrigated on agricultural or forest land via 770. Feed in the form of intermediary animals or a microbial biomass or a processed form of same, may be returned to the animal raising facility 700 via 780. Intermediary animals or fish produced in 800 will be exported for sale or external use via 790.

Figure 22:
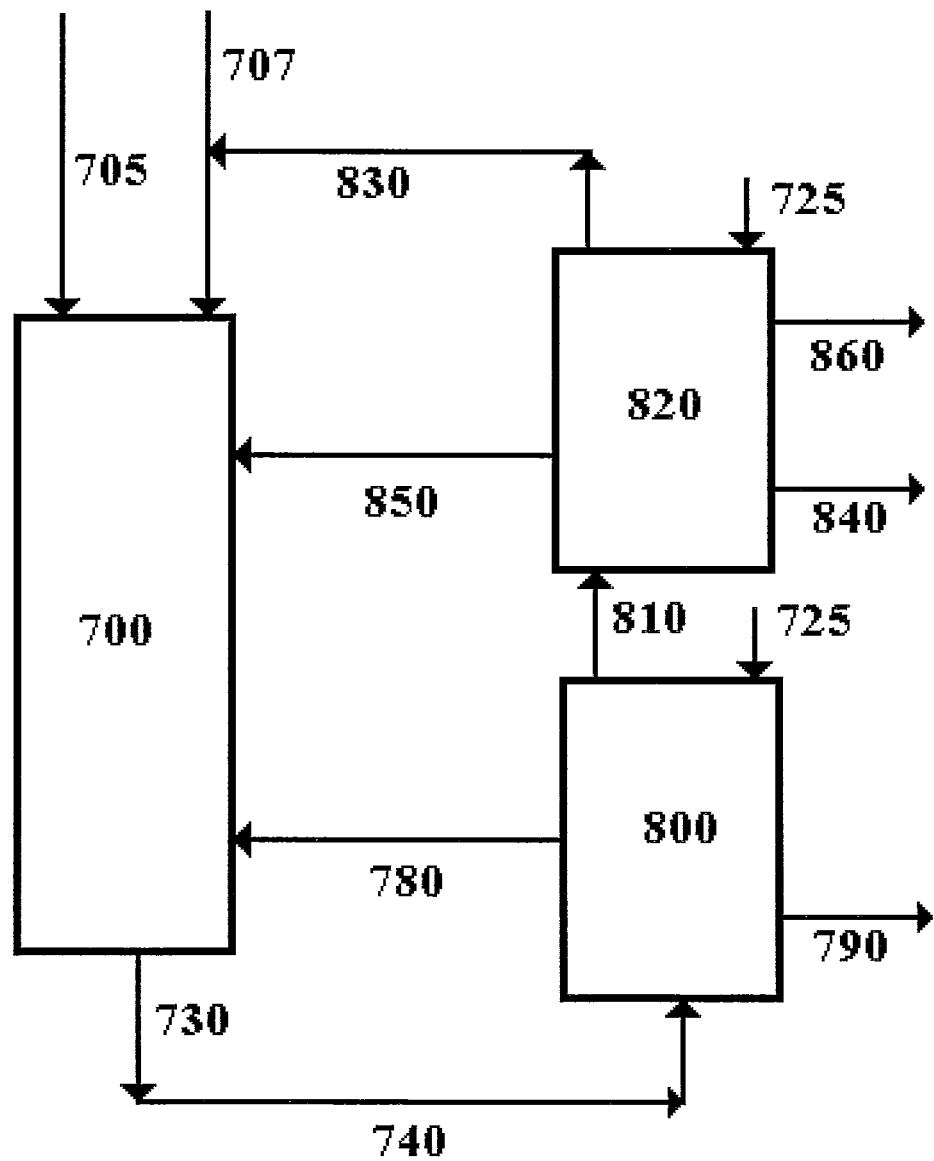
FIG. 22 is a schematic representation of a system in which a recirculating aquaculture system is coupled with an embodiment of the invention as shown in FIG. 1 to perform water treatment, wastewater treatment, waste treatment, feed generation, or some combination of these functions, for the recirculating aquaculture system.

In yet another embodiment of the invention, as shown in FIG. 22, the system as shown in FIG. 1 is added to the system as shown in FIG. 21. As shown in FIG. 22 the recirculating aquaculture system 700 receives inputs of feed 705, and water 707. Water and wastewater containing solid and dissolved wastes are recycled from the recirculating aquaculture system 700 via stream 730 to the system 800. By passing through the Harvested Plant Material Degradation (HPMD) System 4, and the Microbial Growth System 10, as described relative to FIG. 3, the solid and dissolved wastes, particularly including the nutrient fraction of those wastes, will be at least partially removed from the liquid fraction of the recycled stream and will be incorporated within a microbial biomass. Alternatively, by passing through the Combined System 123 or the HPMD zone of the process of the invention, as shown in and described in detail relative to, FIGS. 9*a* & 9*b*, FIGS. 10*a* & 10*b*, FIGS. 11*a* & 11*b*, and FIGS. 12*a* & 12*b*, the solid and dissolved wastes, particularly including the nutrient fraction of those wastes, will be at least partially removed from the liquid fraction of the recycled stream and will be incorporated within a microbial biomass.

Referring again to FIG. 22, the various embodiments of the invention as shown in 800 will receive, as inputs, Harvested Plant Material as previously described and delivered via 725. Effluent water from 800 will be transferred via 810 to 820, which is another embodiment of the process of the invention as shown in, and described in detail in reference to, FIG. 1. The embodiment of the invention as shown in 820 will also receive, as inputs, Harvested Plant Material as previously described and delivered via 725. The microbial processes which occur in the Harvested Plant Material Degradation (HPMD) System 4, and the Microbial Growth System 10, as described relative to, and shown in FIG. 1, will further remove wastes and nutrients from the recirculating stream 810. This further treated stream will then be returned to the animal raising system 700 via the stream 830, or, in the event of excess water within the system, discharged to the environment or irrigated on agricultural or forest land via 840. Feed in the form of intermediary animals or a microbial biomass or a processed form of same, may be returned to the animal raising facility 700 via 850. Some intermediary animals or fish produced in 800 may be exported for sale or external use via 860.

In another embodiment of the present invention, the system may provide a method for creating or discovering microorganisms that are distinct from other known microorganisms, and which may have functional capabilities that are novel or unique. Various different microbes that are created or discovered by the process of this invention, can also be combined to form microbial populations that, as a population, may also have functional capabilities that are novel or unique relative to the known art and science of microbiology. Furthermore, these new populations of microbes can be combined with other known populations of microbes, or with naturally occurring populations of microbes, to form new microbial populations possessing functional capabilities that are novel or unique relative to the known art and science of microbiology.

In the process of the invention an environment suitable for the growth of large numbers of microbes is constructed or is located and defined through the identification of some form of recognizable and functional boundary. This environment, hereafter called the Process Environment, may comprise a liquid environment that is contained within a tank, pond, lagoon, or other constructed structure, or it may comprise a bounded and partially or completely separated part of a naturally occurring lake, stream, ocean, or the like. The Process Environment may also include a non liquid environment such as a building, room, basement, container, tank, pad with or without side walls, depression in the ground, or a flat area of land bounded by a fence, wall, or other delineating device. A non liquid Process Environment may also have liquid periodically or continuously sprayed or irrigated into and onto the environment such that any material contained within the Process Environment may retain moisture or other liquid on the surface or internal to the material itself.

A Process Environment may be constructed or defined relative to some specific Process Objective related to microbial growth and/or activity. The Process Objective may include a desired bioconversion or degradation of some particular substance or group of substances; for example the degradation of a toxic organic compound or the bioconversion of soluble nutrients into a particulate biomass. It may also include the growth of a microbial biomass on a particular substrate; for example the generation of a microbial biomass for use as a feedstock from the bioconversion of cellulose or other plant material. It may include the production via microbial growth or activity of one or more specific compounds from one or more substrates; for example the production of hydrogen or the creation of an antibiotic that has not been known before. It may also include the production of one or more microbial biomasses having particular characteristics; for example the creation of microbes that have rates of mutation that are greater than normal or the creation of microbes that are partially or completely resistant to the effects of toxic compounds.

Once a Process Objective is defined or selected, a Process Environment will be designed to facilitate the creation or discovery of one or more species or types of microbes, or one or more mixed microbial populations, that are able to satisfy the Process Objective. It is an object of the invention that the created or discovered microbes or microbial populations that are obtained as a result of the process of the invention, be able to satisfy the selected Process Objective in a manner that is superior to the known capabilities of existing microbes or microbial populations in the current art and science of microbiology.

The Process Environment designed in reference to the stated Process Objective will be such that it will favor and enhance the growth of microbes and microbial populations which have the greatest likelihood of satisfying the Process Objective or which come as close as possible to satisfying the Process Objective. A suitable substrate for microbial growth, as would be determined by the current art and science of microbiology relative to the Process Objective, is placed within the Process Environment, and other materials also required for microbial growth such as nutrients, oxygen, water, vitamins, or other substances or chemical compounds, are added or made available to any microbes resident within the Process Environment. The Process Environment is then inoculated with samples containing existing microbes obtained from many different sources.

Once a Process Environment has been implemented and inoculated it will be operated and managed for a significant time period. The operation will comprise a series of dynamic processes for the continual or periodic addition of substrates and other materials or compounds such as nutrients that are necessary for microbial growth, and the continual or periodic removal from the Process Environment of various products, by-products, and microbes that are generated by microbial activity. The operation will also comprise the continuation of various dynamic activities, such as mixing, within the Process Environment that facilitate microbial growth and activity, and the dynamic variation of the size, location, or other characteristics of various subenvironments which may be resident within the Process Environment.

The management of the Process Environment may include the continual or periodic monitoring of various process variables such as temperature, pH, conductivity, oxidation reduction potential, or the like, or the concentration of substrates, products, by-products, nutrients, oxygen, microbes, or other constituents. A monitored process variable may serve as a control variable. Thus, if a given process variable deviates from a given set point value or some function of a given set point value, or deviates from a defined range of values, then a control action will be initiated to return the process variable to the desired value or range of values.

The operation and management of a Process Environment may result in a large and diversified microbial population which is itself growing under steady state or exponential growth conditions. Within this population as many constituent microbes as possible should be actively growing and reproducing. This may occur either intermittently or in a steady state or exponential manner.

In a realization of the process of the invention a large diversified microbial population will be growing and reproducing within a specifically designed Process Environment. This will be called an Evolutionary System of the Process Environment. With respect to any given Evolutionary System we define the Evolutionary Momentum of the Evolutionary System as the number of mutations that occur in microbial genomes that are replicating within the corresponding Process Environment per unit of time. Thus the Evolutionary Momentum will be a function of the number of discrete microbial organisms and a function of the individual genomes within those cells, the rate at which the genomes are replicating, and the rate of mutations that occur within those replicating genomes.

In the process of the invention two parameters may be optimized. First, the Evolutionary Momentum must be sufficiently large so that there is a reasonable probability that one or more microbes can mutate to a form that will satisfy the Process Objective of the Process Environment. Second, if such a mutation occurs the Process Environment must be configured in a manner so that the mutant microbe can grow and produce a population that is sufficiently large so that it can be detected within a reasonable amount of time.

It is also understood that the rate at which spontaneous mutations occur in natural populations of microbes is approximately three mutations per every thousand replications of a microbial genome. It is further understood that this natural microbial mutation rate is relatively invariant over a wide range of different microbes with widely varying genome sizes (as measured by the number of nucleotide base pairs per genome) and widely varying growth rates (as measured by doubling times for the microbes). Thus the spontaneous microbial mutation rates themselves only vary by approximately 3-fold, whereas the relative sizes of microbial genomes vary by approximately 6,500-fold and microbial growth rates can vary by over 1,000-fold depending on environmental conditions.

Consider as an example an experiment in which a one gallon bioreactor contains a microbial population with a density of $10^8$ microbes per milliliter (ml) growing with a doubling time of 30 minutes. Substrate and nutrients are being continuously added to the bioreactor, and cells and byproducts are continually being discharged from the bioreactor, so that the resident microbial population is growing at a steady state. Assuming one microbial genome per microbial cell and a spontaneous mutation rate of 0.003 mutations per genome replication, this system would have an Evolutionary Momentum of $3.8 \times 10^5$ mutations per minute (380,000 mutations per minute).

Consider a second example in which a one million gallon Process Environment contains a microbial population with a density of $10^8$ microbes per milliliter (ml) growing with a doubling time of one day. Substrate and nutrients are being continuously added to the Process Environment, and microbial cells and byproducts are continually being discharged from the Process Environment, so that the resident microbial population is growing at a steady state. Again assuming one microbial genome per microbial cell and a spontaneous mutation rate of 0.003 mutations per genome replication, this system would have an Evolutionary Momentum of $7.8 \times 10^{11}$ mutations per minute.

As illustrated by these examples the general embodiment of the process of this invention will have an Evolutionary Momentum greater than one billion mutations per minute and preferably greater than one trillion mutations per minute.

Although the size of the Process Environment, the concentration of microbes, the average growth rate of the microbial population, and the spontaneous mutation rate for microbes are all important variables affecting the Evolutionary Momentum of a Process Environment there are other important factors that also contribute to the process of the invention. One of these concerns methods to enhance the mutation rate within the microbial population.

Alternative means of changing a microbes DNA sequence, often called DNA recombination, can include any of four different mechanisms as follows: 1.) transformation in which DNA one or more fragments not currently part of a microbial cell are taken into a microbial cell and integrated into its DNA genome; 2.) transduction in which a microbial virus carries a segment of its host's DNA into a different microbe that it subsequently infects, and that DNA segment becomes integrated into the second microbe's genome; 3.) conjugation in which one microbe inserts a tubule into a second microbe and injects a DNA fragment into the second microbe such that the DNA fragment becomes integrated into the second microbe's genome; and 4.) plasmid transfer in which a small circular fragment of DNA moves from one microbe to another but does not become integrated into the second microbe's genome. This transfer can occur via Transformation or Conjugation.

The importance of these various mechanisms for DNA recombination relative to the process of the invention is that a given Process Environment can be configured and operated such that these mechanisms are more likely to occur than is the case in normal environments. Since DNA fragments and plasmids are relatively fragile when outside of a microbial cell, action within a Process Environment should be conducted in a manner which will minimize the disruption or destruction of such fragments or plasmids. Similarly, in the case of conjugation tubules connecting two different microbes, action within a Process Environment should be conducted in a manner which will minimize the disruption or destruction of such tubules and the Conjugation process. This will translate into operational methodologies in which variations in pH, temperature, conductivity, oxidation reduction potential, concentration changes, and the like will occur in a slow or non rapid manner. Similarly the Process Environment should be mixed but this mixing again needs to occur in a relatively slow and non violent manner.

In accordance with another embodiment of the present invention, a method comprises harvesting small organisms in a system for producing food and/or feed. The system functions by generating a concentrated microbial biomass from the degradation of harvested plant material, and providing the concentrated microbial biomass for consumption by a small intermediary animal. The small intermediary animal may be fed to a larger production animal, or harvested for feed.

The invention may be applied to a Production System that uses plant material (Plant Material) as previously described. In the method of the invention microbes and part of the microbial biomass are continually or intermittently harvested and removed from the Plant Material. This occurs through the use of small intermediary animals such as small fish, insects, snails, worms, or other macroinvertebrates. These organisms will have continuous or intermittent access to the constrained Plant Material during which time they will collect and consume the microbes.

In the method of the invention the configuration and presentation of the Plant Material to the water, nutrients, and microbes will be such that the microbes will grow on the surface of the Plant Material and form a biofilm covering these surfaces. The Plant Material in general will comprise small pieces or fragments and these will be arranged spatially so that the Small Intermediary Animals can access most or all of the microbial biofilms on the surface area of the Plant Material. The Small Intermediary Animals will be sufficiently mobile so that they can move across the surfaces of the Plant Material and eat and consume the microbes living on these surfaces as they move across them.

In the method of the invention the configuration of the Plant Material pieces and the nature of the Small Intermediary Animals themselves will be such that not all of the microbes living and growing on any given area of the Plant Material surfaces will be consumed at one time by the harvesting organisms. Thus, a microbe consuming organism will move across a given section of Plant Material surface area, harvest and consume large numbers of microbes that are on that surface area. However, the microbe consuming organism will not harvest and consume all of the microbes on the surface area but will leave a reasonable large number of viable microbes behind. This residual biomass will be able to quickly generate a new microbial biomass that will continue the bioconversion of the Plant Material.

Another feature of the microbe harvesting organisms is that as they harvest and consume biofilms and microbial biomasses they will carry some of the microbes that they are consuming with them. These transported microbes will then serve as a microbial inoculum for other Plant Material that the Small Intermediary Animal will subsequently encounter.

As new microbial biomasses grow on the surfaces of the Plant Material they will also be subject to periodic harvesting from other microbe consuming organisms and this cycle will continue to be repeated throughout the operational period of the Production System.

In a number of embodiments of the method of the invention the configuration of the Plant Material in the Production System can be arranged so that the small intermediary animals themselves will be periodically or continually harvested as they consume the microbial biomass. This will occur when larger predatory animals such as fish, crayfish, or the like, which are also living within the Production System environment, encounter the small intermediary animals and consume them for food. This might occur when the Small Intermediary Animals leave the boundaries of the constrained Plant Material or it may occur when the larger animals forage at or within the Plant Material area.

One embodiment of the process of the invention will occur when fish are raised within a Production System for use as human food. In this case the final product organism, the fish, will be given access to the Small Intermediary Animals as they are foraging on the biofilms covering the surfaces of the Plant Material. Thus the fish will harvest and eat the Small Intermediary Animals as they harvest and eat the microbial biofilm that is consuming the appropriately arranged Plant Material.

An example of this embodiment would involve the production of a trout from a food chain consisting of Plant Material as small sticks and brush, to microbes, to snails, to trout. In this case the Production System would contain a submerged brush pile consisting of sticks and brush. Nutrients would be supplied and a microbial biomass or biofilm would grow on the surfaces of the sticks and brush. Snails would be introduced into the Production System and they would form a reproducing population which would feed on the biofilms and microbial biomasses on the surfaces of the sticks and brush. If the brush pile has sufficient spaces between the various constituent sticks and brush then when trout are introduced into the Production System they can swim around and within the submerged brush pile and harvest and eat the snails feeding on the microbial biomass which is eating the brush.

A second embodiment of the process of the invention could involve a situation where the Small Intermediary Animals feed on the microbes consuming the Plant Material and then migrate away from the Plant Material to an area where they themselves are consumed by a larger predatory animal. An example of this embodiment would entail using Plant Material consisting of wood chips as the beginning of the production food chain. The wood chips would be constrained in bats bounded by netting or fencing and only a few inches wide. The netting or fencing would have holes in it sufficiently large to permit easy access to all the chips and the biofilms on their surfaces, by insect larvae and minnows. These insect larvae and minnows would feed on the microbial biofilms that were living on the wood chip surfaces and then the larvae and minnows would occasionally venture out of the constrained bat volumes into more open water where they would be consumed by fish.

If they do not serve as food, for one or more produced aquatic organisms the Small Intermediary Animals may be removed from the Production System by various means. Thus in another embodiment of the process of the invention, the mobility of the organisms themselves will be utilized to facilitate the harvesting process. Thus when a harvest is necessary or desired one or more environmental variables will be adjusted so that the Small Intermediary Animals will leave the constrained Plant Material areas and move to some other area more conducive for their harvest.

For example, if the Small Intermediary Animal is a snail then illuminating one area of the Production System while leaving the remainder of the production volume dark may induce some of the snails to migrate towards the light. If appropriate surfaces are made available to the snails in the illuminated area they will congregate there and then can be easily collected.

In yet another embodiment, the invention comprises a method of balancing a production food chain in a system for producing food or feed from harvested plant material. The food chain production system functions by generating a concentrated microbial biomass from the degradation of harvested plant material, and providing the concentrated microbial biomass for consumption by a small intermediary animal. In a second embodiment of the invention the small intermediary animal may be fed to a larger production animal. Both the Small Intermediary Animal and the larger Production Animal can be harvested for use as food or feed.

The invention is applied to a Production System that uses Plant Material as previously described. In the Production System microbes and part of the microbial biomass are continually or intermittently harvested and removed from the Plant Material. This occurs through the use of Small Intermediary Animals such as small fish, insects, snails, worms, or other macroinvertebrates. These organisms will have continuous or intermittent access to the Plant Material during which time they will collect and consume the microbes.

The configuration of the Plant Material in the Production System is such that the Small Intermediary Animals are periodically or continually harvested as they consume the microbial biomass. This can occur when larger predatory animals such as fish, crayfish, or the like, which may be a part of the Production System environment, encounter the small intermediary animals and consume them for food. Alternatively, the harvesting of Small Intermediary Animals can be performed either mechanically or by utilizing the mobility of the organisms themselves. Thus, when a harvest is necessary or desired, one or more environmental variables could be adjusted so that the Small Intermediary Animals will leave the constrained Plant Material areas and move to some other area conducive for their harvest. A second alternative could entail the removal of some or all of the Plant Material from the Production System, removing some of the Small Intermediary Animals by a physical means such as flushing with water or shaking, and then returning the Plant Material back into the Production System.

The method of this invention comprises a procedure to optimize the growth and harvesting of the final Production Animal from the Production System. The final Production Animal may be a Small Intermediary Animal or it may be a larger animal which consumes some or all of the Small Intermediary Animals for food. In either case, its growth and harvesting need to be managed such that imbalances in the food production chain do not occur. To achieve the objective of optimizing the production of the final Production Animal, the entire food chain must be monitored and managed to maintain balance. If this does not occur, decreases in production rates will occur.

For example, if too many Small Intermediary Animals are allowed to accumulate, they can harvest too much of the microbial biomass. This will then decrease the rate of Plant Material utilization and new microbial biomass generation. The lack of an adequate food supply for the Small Intermediary Animals will cause their production rate to fall and this will lead to smaller final Production Animal harvests. The entire food chain production rate will slow down.

To avoid this situation the method of the invention comprises a procedure for monitoring and regulating the growth of all component organisms within the food chain. This procedure relies on both direct measurements and inferential reasoning to keep all component organisms growing at desirable rates. It begins with a measure of the plant material initially used to start the Production System.

The Plant Material will serve as the source of carbon and energy for the production process. A bioconversion rate will be selected to degrade all or some fraction of the initial Plant Material loading to the system, over a defined period of time. The rate selected will be a function of the microbial growth rate that can be sustained on the Plant Material. This will factor in the surface to weight ratio for the average Plant Material particle size (either as chips, branches, or the like), the weight of sustainable biomass per unit of Plant Material surface area, and a practical average growth rate for the microbial population as a whole. Based on these considerations, a nutrient feed rate for nitrogen and phosphorus will be calculated and applied to the Production System.

Water quality will be monitored to ensure that the nutrient additions are all being consumed by the microbial biomass. This will entail frequent measures of the concentrations of nitrogen and phosphorus forms at specific monitoring points within the Production System. The nitrogen and phosphorus concentrations that would occur, if the regular nutrient additions made to the Production System were made to a volume of water equal to the volume of the Production System, will be calculated. This value, or a function of this value, will be used as a control variable to set target trending values for the concentration of various nutrient forms at the monitoring points.

In yet another embodiment of the present invention, a method comprises producing food, energy, and clean water through the application of an environmental technology platform. Use of the technology platform to produce food and energy may result in the production of clean fresh water which can be sequestered within forest environments. It will also result in the sequestration of large quantities of carbon within restored forest habitat and this can significantly reduce the carbon dioxide concentration in the atmosphere, thereby mitigating one of the largest factors in global climate change.

This invention comprises a method of harvesting small organisms in a system for producing food and/or feed. The system functions by generating a concentrated microbial biomass from the degradation of harvested plant material and providing the concentrated microbial biomass for consumption by a small intermediary animal. The small intermediary animal may be fed to a larger production animal such as a fish, or harvested directly for food or feed. Usually the food and feed production process does not bioconvert all of the harvested plant material. Since the remaining plant material residue has a relatively higher energy content than the originating Plant Material, it is usually processed and used as a substrate for energy production.

While the processes of the invention can use any plant material (Plant Material) produced by a photosynthetic reaction, it generally will utilize Plant Material grown in forests or woodlots and will include whole trees and bushes, logs, branches, leaves, and roots. However, Plant Material may also be utilized that is produced within aquatic environments and could include algae, phytoplankton, seaweeds, and a variety of other higher aquatic plants. Plant Material such as grasses, reeds, shrubs, bushes, yard wastes, and a variety of agricultural products and byproducts such as corn stover, straw, hay, vegetable and fruit processing waste, etc. may also be used in the processes of this invention. Plant Material may also include various produced or manufactured materials and products such as lumber, paper, cardboard, fabric, and the like.

The various embodiments of the processes of this invention are usually manifested in a Production System wherein Plant Material is collected and placed in a container, pond, tank, or the like, or is piled or placed on a pad or in a contained area where liquid emanating from the material can be collected. Usually, the Plant Material is introduced in small particles that have a relatively high surface to volume ratio. The Plant Material is subjected to a microbial treatment process in which various constituents of the Plant Material are converted into a microbial cell mass. Nutrients such as nitrogen and phosphorus are periodically or continually introduced into the Production System to facilitate the growth of the microbial biomass.

In the methods of the invention, microbes and parts of the microbial biomass are continually or intermittently harvested and removed from the Plant Material. This usually occurs as a result of the feeding activity of small intermediary animals. Such small intermediary animals are then harvested via a variety of means or are consumed by a larger product animal which will in turn be harvested and used for food or feed.

Once the microbial conversion and treatment process has progressed to a desired level of production of microbes and higher animals, the remaining material (designated hereafter as the Biologically Processed Material) is collected and prepared for energy production. This preparation process may include rinsing, irrigating, hosing, or other methods of cleaning the material to remove nutrients, residual microbes, and other larger organisms.

The resulting Biologically Processed Material may comprise a different distribution of component compounds than will the Plant Material from which it was produced. Thus, the Biologically Processed Material will contain relatively fewer nutrients, proteins, nucleic acids, sugars, starches, fats, oils, and other readily degradable substances than the original Plant Material. The Biologically Processed Material will also contain relatively less cellulose and hemicellulose, and relatively more lignin, than will the source Plant Material. Consequently the Biologically Processed Material will have a significantly higher heat value per unit of dry weight than will the source Plant Material.

The Biologically Processed Material may be a desirable energy substrate that can be used as a feedstock for incineration or combustion to provide heat to run a generator or fire a boiler. It may also be used as a feedstock for a pyrolytic, gasification, or liquification process in which a variety of other usable energy products, as well as heat, may be produced. The useable energy products could include carbon, charcoal, alcohols, liquid oils, and burnable gases such as methane or a variety of mixtures of methane, hydrogen, and carbon monoxide.

The general processes of the technology platform can further act as water and wastewater treatment systems, particularly with respect to eliminating nutrient pollution in water. This may occur through the direct action of the production process by which plant material is bioconverted into foods and feeds, or it may occur as a result of the establishment and management of wetlands within forest environments used for the production of the Plant Material used within the Production Systems.

The use of natural habitats, such as forests, as the primary source of harvested Plant Material for the processes of the invention has additional environmental benefits. Producing foods and feeds from a mixed and diverse community of plants, which grow in environments that are not plowed, mechanically cultivated, or contacted with pesticides and/or excessive quantities of fertilizers, eliminates pollution which occurs as a result of these practices. Erosion is minimized and the nutrient and pesticide pollution associated with non point source agricultural runoff can be significantly limited. Also Plant Material can be periodically harvested from an environment and this can be performed at a time and in a manner that minimizes the disruption of wildlife that uses that environment. In addition to the environmental benefits the integrated technology platform also offers health and safety benefits because of the ability to produce non-contaminated fish and other seafood products.

What is claimed is:

1. An apparatus for growing a microbial population, comprising:
    a bounded tank comprising water and a diversified microbial population comprising constituent microbes within the water, the bounded tank having an upper end and a bottom surface generally opposite the upper end, the bounded tank defining a lower fluid zone within the water and adjacent the bottom surface, and an upper fluid zone adjacent the upper end, wherein a population of constituent microbes is concentrated in the lower fluid zone;
    a substrate of wood chips for promoting the growth and reproduction of constituent microbes, wherein the substrate of wood chips is provided in fluid contact with the water of the bounded tank;
    a pump for creating movement of the constituent microbes within the water of the bounded tank, the pump having an inlet provided adjacent the bottom surface of the bounded tank;
    a transfer line connected to the pump, the transfer line having an outlet adjacent the substrate of wood chips for directing an effluent taken from the lower fluid zone of the bounded tank through at least a portion of the substrate of wood chips,
    wherein the substrate of wood chips is located remote from the bounded tank, and wherein the transfer line directs an effluent taken from the lower fluid zone of the bounded tank to the remote substrate of wood chips.

2. The apparatus of claim 1, further comprising a process monitor in communication with the microbial population.

3. The apparatus of claim 1, wherein the process monitor includes at least one of a temperature monitor, a pH monitor, a conductivity monitor, and an oxidation reduction potential monitor.

4. The apparatus of claim 1, wherein the substrate of wood chips is contained within a bat structure and at least partially submerged within the water of the bounded tank.

5. The apparatus of claim 1, wherein the substrate of wood chips is at least partially suspended over the bounded tank.

6. The apparatus of claim 5, wherein the transfer line directs an effluent taken from the lower fluid zone of the bounded tank to the substrate of wood chips at least partially suspended over the bounded tank.

7. The apparatus of claim 6, wherein excess water exiting the substrate of wood chips is returned to the bounded tank.

8. The apparatus of claim 6, wherein excess water exiting the substrate of wood chips is directed to a fish raising platform having fish therein.

9. The apparatus of claim 1, wherein fish are provided within the upper fluid zone.

10. A process for growing a microbial population, comprising:
    providing a bounded tank comprising water and a diversified microbial population comprising constituent microbes within the water, the bounded tank comprising an upper fluid zone and a lower fluid zone within the bounded tank;
    concentrating a population of constituent microbes in the lower fluid zone;
    contacting a substrate of wood chips for promoting growth and reproduction of constituent microbes with water from the lower fluid zone of the bounded tank, and
    wherein excess water exiting the substrate of wood chips is directed to a fish raising platform having fish therein.

11. The process of claim 10, wherein the substrate of wood chips is at least partially suspended over the bounded tank, and wherein excess water exiting the substrate of wood chips is returned to the bounded tank.

12. The process of claim 10, wherein the substrate of wood chips is contained within a bat structure and at least partially submerged within the water of the bounded tank.

13. The process of claim 10, further comprising providing fish within the upper fluid zone of the bounded tank.

14. A process for growing a microbial population, comprising:
    providing a bounded tank comprising water and a diversified microbial population comprising constituent microbes within the water, the bounded tank comprising an upper fluid zone and a lower fluid zone within the bounded tank;
    concentrating a population of constituent microbes in the lower fluid zone;
    contacting a substrate of wood chips for promoting growth and reproduction of constituent microbes with water from the lower fluid zone of the bounded tank, and
    wherein the substrate of wood chips is contained within a bat structure and at least partially submerged within the water of the bounded tank.

15. The process of claim 14, further comprising providing fish within the upper fluid zone of the bounded tank.

* * * * *